United States Patent
Aljuri et al.

(10) Patent No.: US 11,172,986 B2
(45) Date of Patent: Nov. 16, 2021

(54) ABLATION WITH ENERGY CARRIED IN FLUID STREAM

(71) Applicant: AQUABEAM LLC, Hillsborough, CA (US)

(72) Inventors: Nikolai Aljuri, Hillsborough, CA (US); Rodney C. Perkins, Woodside, CA (US)

(73) Assignee: AQUABEAM LLC, Hillsborough, CA (US)

( * ) Notice: Subject to any disclaimer, the term of this patent is extended or adjusted under 35 U.S.C. 154(b) by 0 days.

(21) Appl. No.: 16/894,413

(22) Filed: Jun. 5, 2020

(65) Prior Publication Data

US 2020/0323590 A1 Oct. 15, 2020

Related U.S. Application Data

(63) Continuation of application No. 16/382,631, filed on Apr. 12, 2019, now Pat. No. 11,033,330, which is a
(Continued)

(51) Int. Cl.
*A61B 18/20* (2006.01)
*A61C 1/00* (2006.01)
(Continued)

(52) U.S. Cl.
CPC ........ *A61B 18/20* (2013.01); *A61B 17/32037* (2013.01); *A61C 1/0046* (2013.01);
(Continued)

(58) Field of Classification Search
CPC ... A61B 18/20; A61B 17/32037; A61B 18/24; A61B 2017/00274; A61B 2018/00547; A61B 2018/00565; A61B 2018/00577; A61B 2018/00601; A61B 2018/206; A61C 1/0046; A61C 17/0202
(Continued)

(56) References Cited

U.S. PATENT DOCUMENTS

| 3,763,860 A | 10/1973 | Clarke |
| 3,818,913 A | 6/1974 | Wallach |

(Continued)

FOREIGN PATENT DOCUMENTS

| CA | 2330436 A1 | 11/2009 |
| CN | 1137230 A | 12/1996 |

(Continued)

OTHER PUBLICATIONS

Nishimura, et al. Similarity Law on Shedding Frequency of Cavitation Cloud Induced by a Cavitating Jet. Journal of Fluid Science and Technology, vol. 7, No. 3, 2012, pp. 405-420.
(Continued)

*Primary Examiner* — Aaron F Roane
(74) *Attorney, Agent, or Firm* — Fisherbroyles LLP; John Shimmick

(57) ABSTRACT

Methods and systems for modifying tissue use a pressurized fluid stream carrying coherent light energy. The methods and systems may be used for resecting and debulking soft and hard biological tissues. The coherent light is focused within a stream of fluid to deliver energy to the tissue to be treated.

15 Claims, 12 Drawing Sheets

Related U.S. Application Data continuation of application No. 14/336,606, filed on Jul. 21, 2014, now Pat. No. 10,342,615, which is a continuation of application No. 12/399,585, filed on Mar. 6, 2009, now Pat. No. 8,814,921.

(60) Provisional application No. 61/097,497, filed on Sep. 16, 2008, provisional application No. 61/034,412, filed on Mar. 6, 2008.

(51) Int. Cl.
*A61C 17/02* (2006.01)
*A61B 17/3203* (2006.01)
*A61B 18/24* (2006.01)
*A61B 17/00* (2006.01)
*A61B 18/00* (2006.01)

(52) U.S. Cl.
CPC .......... *A61C 17/0202* (2013.01); *A61B 18/24* (2013.01); *A61B 2017/00274* (2013.01); *A61B 2018/00547* (2013.01); *A61B 2018/00565* (2013.01); *A61B 2018/00577* (2013.01); *A61B 2018/00601* (2013.01); *A61B 2018/206* (2013.01)

(58) Field of Classification Search
USPC .......................................................... 606/10
See application file for complete search history.

(56) References Cited

U.S. PATENT DOCUMENTS

| | | |
|---|---|---|
| 3,821,510 A | 6/1974 | Muncheryan |
| 3,847,988 A | 11/1974 | Gold |
| 3,875,229 A | 4/1975 | Gold |
| 4,024,866 A | 5/1977 | Wallach |
| 4,040,413 A | 8/1977 | Ohshiro |
| 4,097,578 A | 6/1978 | Perronnet |
| 4,198,960 A | 4/1980 | Utsugi |
| 4,220,735 A | 9/1980 | Dieck |
| 4,239,776 A | 12/1980 | Bayles |
| 4,377,584 A | 3/1983 | Rasmusson |
| 4,386,080 A | 5/1983 | Crossley |
| 4,461,283 A | 7/1984 | Doi |
| 4,470,407 A | 9/1984 | Hussein |
| 4,474,251 A | 10/1984 | Johnson, Jr. |
| 4,532,935 A | 8/1985 | Wang |
| 4,560,373 A | 12/1985 | Sugino |
| 4,597,388 A | 7/1986 | Koziol |
| 4,636,505 A | 1/1987 | Tucker |
| 4,672,963 A | 6/1987 | Barken |
| 4,685,458 A | 8/1987 | Leckrone |
| 4,747,405 A | 5/1988 | Leckrone |
| 4,760,071 A | 7/1988 | Rasmusson |
| 4,776,349 A | 10/1988 | Nashef |
| 4,854,301 A | 8/1989 | Nakajima |
| 4,898,574 A | 2/1990 | Uchiyama |
| 4,905,673 A | 3/1990 | Pimiskern |
| 4,913,698 A | 4/1990 | Ito |
| 4,983,165 A | 1/1991 | Loiterman |
| 5,029,574 A | 7/1991 | Shimamura |
| 5,037,431 A | 8/1991 | Summers |
| 5,085,659 A | 2/1992 | Rydell |
| 5,116,615 A | 5/1992 | Gokcen |
| 5,135,482 A | 8/1992 | Neracher |
| 5,196,023 A | 3/1993 | Martin |
| 5,207,672 A | 5/1993 | Roth |
| 5,217,465 A | 6/1993 | Steppe |
| 5,257,991 A | 11/1993 | Fletcher |
| 5,267,341 A | 11/1993 | Shearin |
| 5,269,785 A | 12/1993 | Bonutti |
| 5,308,323 A | 5/1994 | Sogawa |
| 5,318,589 A | 6/1994 | Lichtman |
| 5,322,503 A | 6/1994 | Desai |
| 5,322,504 A | 6/1994 | Doherty |
| 5,325,848 A | 7/1994 | Adams |
| 5,338,292 A * | 8/1994 | Clement ................ A61B 10/04 604/22 |
| 5,342,381 A | 8/1994 | Tidemand |
| 5,344,395 A | 9/1994 | Whalen |
| 5,353,783 A | 10/1994 | Nakao |
| 5,370,609 A | 12/1994 | Drasler |
| 5,372,124 A | 12/1994 | Takayama |
| 5,411,016 A | 5/1995 | Kume |
| 5,425,735 A | 6/1995 | Rosen |
| 5,431,649 A | 7/1995 | Mulier |
| 5,441,485 A | 8/1995 | Peters |
| 5,449,356 A | 9/1995 | Walbrink |
| 5,450,843 A | 9/1995 | Moll |
| 5,454,782 A | 10/1995 | Perkins |
| 5,472,406 A | 12/1995 | De La Torre |
| 5,472,426 A | 12/1995 | Bonati |
| 5,496,267 A | 3/1996 | Drasler |
| 5,496,309 A | 3/1996 | Saadat |
| 5,501,667 A | 3/1996 | Verduin, Jr. |
| 5,505,729 A | 4/1996 | Rau |
| 5,514,669 A | 5/1996 | Selman |
| 5,520,684 A | 5/1996 | Imran |
| 5,527,330 A | 6/1996 | Tovey |
| 5,545,170 A | 8/1996 | Hart |
| 5,562,648 A | 10/1996 | Peterson |
| 5,562,678 A | 10/1996 | Booker |
| 5,562,703 A | 10/1996 | Desai |
| 5,572,999 A | 11/1996 | Funda |
| 5,573,535 A | 11/1996 | Viklund |
| 5,592,942 A | 1/1997 | Webler |
| 5,613,973 A | 3/1997 | Jackson |
| 5,620,414 A | 4/1997 | Campbell, Jr. |
| 5,630,794 A | 5/1997 | Lax |
| 5,645,083 A | 7/1997 | Essig |
| 5,649,923 A | 7/1997 | Gregory |
| 5,653,374 A | 8/1997 | Young |
| 5,658,311 A | 8/1997 | Baden |
| 5,662,590 A | 9/1997 | De La Torre |
| 5,666,954 A | 9/1997 | Chapelon |
| 5,672,153 A | 9/1997 | Lax |
| 5,672,171 A | 9/1997 | Andrus |
| 5,674,226 A | 10/1997 | Doherty |
| 5,695,500 A | 12/1997 | Taylor |
| 5,697,949 A | 12/1997 | Giurtino |
| 5,710,870 A | 1/1998 | Ohm |
| 5,716,325 A | 2/1998 | Bonutti |
| 5,753,641 A | 5/1998 | Gormley |
| 5,770,603 A | 6/1998 | Gibson |
| 5,772,657 A | 6/1998 | Hmelar |
| 5,773,791 A | 6/1998 | Kuykendal |
| 5,782,848 A | 7/1998 | Lennox |
| 5,785,521 A | 7/1998 | Rizoiu |
| 5,788,667 A | 8/1998 | Stoller |
| 5,792,165 A | 8/1998 | Klieman |
| 5,795,153 A | 8/1998 | Rechmann |
| 5,797,900 A | 8/1998 | Madhani |
| 5,810,770 A | 9/1998 | Chin |
| 5,817,649 A | 10/1998 | Labrie |
| 5,833,701 A | 11/1998 | Gordon |
| 5,836,909 A | 11/1998 | Cosmescu |
| 5,836,941 A | 11/1998 | Yoshihara |
| 5,861,002 A | 1/1999 | Desai |
| 5,871,462 A | 2/1999 | Yoder |
| 5,872,150 A | 2/1999 | Elbrecht |
| 5,893,869 A | 4/1999 | Barnhart |
| 5,897,491 A | 4/1999 | Kastenbauer |
| 5,902,499 A | 5/1999 | Richerzhagen |
| 5,907,893 A | 6/1999 | Zadno-Azizi |
| 5,924,175 A | 7/1999 | Lippitt |
| 5,989,230 A | 11/1999 | Frassica |
| 5,994,362 A | 11/1999 | Gormley |
| 6,022,860 A | 2/2000 | Engel |
| 6,033,371 A | 3/2000 | Torre |
| 6,066,130 A | 5/2000 | Gregory |
| 6,071,281 A | 6/2000 | Burnside |
| 6,071,284 A | 6/2000 | Fox |
| 6,093,157 A | 7/2000 | Chandrasekaran |

(56) References Cited

U.S. PATENT DOCUMENTS

| | | | |
|---|---|---|---|
| 6,110,171 A | 8/2000 | Rydell | |
| 6,117,128 A | 9/2000 | Gregory | |
| 6,120,476 A | 9/2000 | Fung | |
| 6,120,498 A | 9/2000 | Jani | |
| 6,135,993 A | 10/2000 | Hussman | |
| 6,142,991 A | 11/2000 | Schatzberger | |
| 6,156,030 A | 12/2000 | Neev | |
| 6,174,318 B1 | 1/2001 | Bates | |
| 6,179,831 B1 | 1/2001 | Bliweis | |
| 6,183,435 B1 | 2/2001 | Bumbalough | |
| 6,200,573 B1 | 3/2001 | Locke | |
| 6,206,903 B1 | 3/2001 | Ramans | |
| 6,216,573 B1 * | 4/2001 | Moutafis | A61B 17/3203 417/413.1 |
| 6,217,543 B1 | 4/2001 | Anis | |
| 6,217,860 B1 | 4/2001 | Woo | |
| 6,228,046 B1 | 5/2001 | Brisken | |
| 6,231,591 B1 | 5/2001 | Desai | |
| 6,254,597 B1 | 7/2001 | Rizoiu | |
| 6,296,639 B1 | 10/2001 | Truckai | |
| 6,322,557 B1 | 11/2001 | Nikolaevich | |
| 6,326,616 B1 | 12/2001 | Andrien, Jr. | |
| 6,375,635 B1 * | 4/2002 | Moutafis | A61B 17/3203 604/22 |
| 6,378,525 B1 | 4/2002 | Beyar | |
| 6,394,998 B1 | 5/2002 | Wallace | |
| 6,398,792 B1 | 6/2002 | O'Connor | |
| 6,405,078 B1 | 6/2002 | Moaddeb | |
| 6,406,486 B1 | 6/2002 | De La Torre | |
| 6,413,256 B1 | 7/2002 | Truckai | |
| 6,425,877 B1 | 7/2002 | Edwards | |
| 6,436,107 B1 | 8/2002 | Wang | |
| 6,440,061 B1 | 8/2002 | Wenner | |
| 6,440,105 B1 | 8/2002 | Menne | |
| 6,451,017 B1 | 9/2002 | Moutafis | |
| 6,505,629 B1 | 1/2003 | Mikus | |
| 6,508,823 B1 | 1/2003 | Gonon | |
| 6,522,906 B1 | 2/2003 | Salisbury, Jr. | |
| 6,524,270 B1 | 2/2003 | Bolmsjö | |
| 6,554,793 B1 | 4/2003 | Pauker | |
| 6,565,555 B1 | 5/2003 | Ryan | |
| 6,572,578 B1 | 6/2003 | Blanchard | |
| 6,577,891 B1 | 6/2003 | Jaross | |
| 6,602,227 B1 | 8/2003 | Cimino | |
| 6,607,524 B1 | 8/2003 | LaBudde | |
| 6,638,246 B1 | 10/2003 | Naimark | |
| 6,671,581 B2 | 12/2003 | Niemeyer | |
| 6,676,668 B2 | 1/2004 | Mercereau | |
| 6,685,698 B2 | 2/2004 | Morley | |
| 6,706,050 B1 | 3/2004 | Giannadakis | |
| 6,720,745 B2 | 4/2004 | Lys | |
| 6,736,784 B1 | 5/2004 | Menne | |
| 6,763,259 B1 | 7/2004 | Hauger | |
| 6,814,731 B2 | 11/2004 | Swanson | |
| 6,821,275 B2 | 11/2004 | Truckai | |
| 6,890,332 B2 | 5/2005 | Truckai | |
| 6,905,475 B2 | 6/2005 | Hauschild | |
| 6,953,461 B2 | 10/2005 | McClurken | |
| 6,960,182 B2 | 11/2005 | Moutafis | |
| 6,986,764 B2 | 1/2006 | Davenport | |
| 7,015,253 B2 | 3/2006 | Escandon | |
| 7,087,061 B2 | 8/2006 | Chernenko | |
| 7,115,100 B2 | 10/2006 | McRury | |
| 7,122,017 B2 | 10/2006 | Moutafis | |
| 7,163,875 B2 | 1/2007 | Richerzhagen | |
| 7,282,055 B2 | 10/2007 | Tsuruta | |
| 7,320,594 B1 | 1/2008 | Rizoiu | |
| 7,326,054 B2 | 2/2008 | Todd | |
| 7,344,528 B1 | 3/2008 | Tu | |
| 7,351,193 B2 | 4/2008 | Forman | |
| 7,556,632 B2 | 7/2009 | Zadno | |
| 7,559,934 B2 | 7/2009 | Teague | |
| 7,594,900 B1 | 9/2009 | Nash | |
| 7,725,214 B2 | 5/2010 | Diolaiti | |
| 7,736,356 B2 | 6/2010 | Cooper | |
| 7,882,841 B2 | 2/2011 | Aljuri | |
| 7,883,475 B2 | 2/2011 | Dupont | |
| 7,963,911 B2 | 6/2011 | Turliuc | |
| 7,967,799 B2 | 6/2011 | Boukhny | |
| 7,987,046 B1 | 7/2011 | Peterman | |
| 8,002,713 B2 | 8/2011 | Heske | |
| 8,038,598 B2 | 10/2011 | Khachi | |
| 8,049,873 B2 | 11/2011 | Hauger | |
| 8,092,397 B2 | 1/2012 | Wallace | |
| 8,092,507 B2 | 1/2012 | Tomasello | |
| 8,187,173 B2 | 5/2012 | Miyoshi | |
| 8,224,484 B2 | 7/2012 | Swarup | |
| 8,257,303 B2 | 9/2012 | Moll | |
| 8,414,564 B2 | 4/2013 | Goldshleger | |
| 8,480,595 B2 | 7/2013 | Speeg | |
| 8,518,024 B2 | 8/2013 | Williams | |
| 8,523,762 B2 | 9/2013 | Miyamoto | |
| 8,540,748 B2 | 9/2013 | Murphy | |
| 8,795,194 B2 | 8/2014 | Howard | |
| 8,801,702 B2 | 8/2014 | Hoey | |
| 8,814,921 B2 | 8/2014 | Aljuri | |
| 8,820,603 B2 | 9/2014 | Shelton, IV | |
| 8,827,948 B2 | 9/2014 | Romo | |
| 8,882,660 B2 | 11/2014 | Phee | |
| 8,945,163 B2 | 2/2015 | Voegele | |
| 8,956,280 B2 | 2/2015 | Eversull | |
| 9,173,713 B2 | 11/2015 | Hart | |
| 9,232,959 B2 | 1/2016 | Aljuri | |
| 9,232,960 B2 | 1/2016 | Aljuri | |
| 9,237,902 B2 | 1/2016 | Aljuri | |
| 9,254,123 B2 | 2/2016 | Alvarez | |
| 9,345,456 B2 | 5/2016 | Tsonton | |
| 9,364,250 B2 | 6/2016 | Aljuri | |
| 9,364,251 B2 | 6/2016 | Aljuri | |
| 9,460,536 B2 | 10/2016 | Hasegawa | |
| 9,504,604 B2 | 11/2016 | Alvarez | |
| 9,510,852 B2 | 12/2016 | Aljuri | |
| 9,510,853 B2 | 12/2016 | Aljuri | |
| 9,561,083 B2 | 2/2017 | Yu | |
| 9,592,042 B2 | 3/2017 | Titus | |
| 9,597,152 B2 | 3/2017 | Schaeffer | |
| 9,622,827 B2 | 4/2017 | Yu | |
| 9,636,184 B2 | 5/2017 | Lee | |
| 9,668,764 B2 | 6/2017 | Aljuri | |
| 9,713,509 B2 | 7/2017 | Schuh | |
| 9,727,963 B2 | 8/2017 | Mintz | |
| 9,730,757 B2 | 8/2017 | Brudniok | |
| 9,737,371 B2 | 8/2017 | Romo | |
| 9,737,373 B2 | 8/2017 | Schuh | |
| 9,744,335 B2 | 8/2017 | Jiang | |
| 9,763,741 B2 | 9/2017 | Alvarez | |
| 9,788,910 B2 | 10/2017 | Schuh | |
| 9,844,412 B2 | 12/2017 | Bogusky | |
| 9,867,635 B2 | 1/2018 | Alvarez | |
| 9,867,636 B2 | 1/2018 | Mcleod | |
| 9,918,681 B2 | 3/2018 | Wallace | |
| 9,931,025 B1 | 4/2018 | Graetzel | |
| 9,931,445 B2 | 4/2018 | Pustilnik | |
| 9,949,749 B2 | 4/2018 | Noonan | |
| 9,955,986 B2 | 5/2018 | Shah | |
| 9,962,228 B2 | 5/2018 | Schuh | |
| 9,980,785 B2 | 5/2018 | Schuh | |
| 9,993,313 B2 | 6/2018 | Schuh | |
| 10,016,900 B1 | 7/2018 | Meyer | |
| 10,022,192 B1 | 7/2018 | Ummalaneni | |
| 10,080,576 B2 | 9/2018 | Romo | |
| 10,136,959 B2 | 11/2018 | Mintz | |
| 10,145,747 B1 | 12/2018 | Lin | |
| 10,149,720 B2 | 12/2018 | Romo | |
| 10,159,532 B1 | 12/2018 | Ummalaneni | |
| 10,159,533 B2 | 12/2018 | Moll | |
| 10,169,875 B2 | 1/2019 | Mintz | |
| 10,231,867 B2 | 3/2019 | Alvarez | |
| 10,251,665 B2 | 4/2019 | Aljuri | |
| 10,321,931 B2 | 6/2019 | Aljuri | |
| 10,342,615 B2 | 7/2019 | Aljuri | |
| 10,482,599 B2 | 11/2019 | Mintz | |
| 10,517,692 B2 | 12/2019 | Eyre | |
| 10,524,866 B2 | 1/2020 | Srinivasan | |

(56) References Cited

U.S. PATENT DOCUMENTS

| | | | |
|---|---|---|---|
| 10,639,114 B2 | 5/2020 | Schuh | |
| 10,653,438 B2 | 5/2020 | Aljuri | |
| 2001/0048942 A1 | 12/2001 | Weisman | |
| 2002/0010502 A1 | 1/2002 | Trachtenberg | |
| 2002/0019644 A1 | 2/2002 | Hastings | |
| 2002/0022869 A1 | 2/2002 | Hareyama | |
| 2002/0040220 A1 | 4/2002 | Zvuloni | |
| 2002/0042620 A1* | 4/2002 | Julian | A61B 34/76 606/130 |
| 2002/0111608 A1 | 8/2002 | Baerveldt et al. | |
| 2002/0111617 A1 | 8/2002 | Cosman | |
| 2002/0111621 A1 | 8/2002 | Wallace | |
| 2002/0128637 A1 | 9/2002 | von der Heide | |
| 2002/0183735 A1 | 12/2002 | Edwards | |
| 2003/0004455 A1 | 1/2003 | Kadziauskas | |
| 2003/0036768 A1 | 2/2003 | Hutchins | |
| 2003/0040681 A1 | 2/2003 | Ng | |
| 2003/0060813 A1 | 3/2003 | Loeb | |
| 2003/0060819 A1 | 3/2003 | McGovern | |
| 2003/0065321 A1 | 4/2003 | Carmel | |
| 2003/0065358 A1 | 4/2003 | Frecker | |
| 2003/0073902 A1 | 4/2003 | Hauschild | |
| 2003/0073920 A1 | 4/2003 | Smits | |
| 2003/0109877 A1 | 6/2003 | Morley | |
| 2003/0109889 A1 | 6/2003 | Mercereau | |
| 2003/0135205 A1 | 7/2003 | Davenport | |
| 2003/0139041 A1 | 7/2003 | LeClair | |
| 2003/0158545 A1 | 8/2003 | Hovda | |
| 2003/0199860 A1 | 10/2003 | Loeb | |
| 2003/0208189 A1 | 11/2003 | Payman | |
| 2003/0216722 A1 | 11/2003 | Swanson | |
| 2004/0030349 A1 | 2/2004 | Boukhny | |
| 2004/0059216 A1 | 3/2004 | Vetter et al. | |
| 2004/0097829 A1 | 5/2004 | McRury | |
| 2004/0133254 A1 | 7/2004 | Sterzer | |
| 2004/0143253 A1 | 7/2004 | Vanney | |
| 2004/0153093 A1 | 8/2004 | Donovan | |
| 2004/0158261 A1 | 8/2004 | Vu | |
| 2004/0186349 A1 | 9/2004 | Ewers | |
| 2004/0193146 A1 | 9/2004 | Lee | |
| 2004/0210116 A1 | 10/2004 | Nakao | |
| 2004/0215294 A1 | 10/2004 | Littrup | |
| 2004/0253079 A1 | 12/2004 | Sanchez | |
| 2005/0004516 A1 | 1/2005 | Vanney | |
| 2005/0010205 A1 | 1/2005 | Hovda | |
| 2005/0033270 A1 | 2/2005 | Ramans | |
| 2005/0054900 A1 | 3/2005 | Mawn | |
| 2005/0054994 A1 | 3/2005 | Cioanta | |
| 2005/0070844 A1 | 3/2005 | Chow | |
| 2005/0159645 A1 | 7/2005 | Bertolero | |
| 2005/0159676 A1 | 7/2005 | Taylor | |
| 2005/0165383 A1 | 7/2005 | Eshel | |
| 2005/0192652 A1 | 9/2005 | Cioanta | |
| 2005/0240178 A1 | 10/2005 | Morley | |
| 2005/0256517 A1 | 11/2005 | Boutoussov | |
| 2005/0261705 A1 | 11/2005 | Gist | |
| 2005/0288639 A1 | 12/2005 | Hibner | |
| 2005/0288665 A1 | 12/2005 | Woloszko | |
| 2006/0015133 A1 | 1/2006 | Grayzel | |
| 2006/0030787 A1 | 2/2006 | Quay | |
| 2006/0058813 A1 | 3/2006 | Teague | |
| 2006/0089626 A1 | 4/2006 | Vlegele | |
| 2006/0116693 A1 | 6/2006 | Weisenburgh | |
| 2006/0129125 A1 | 6/2006 | Copa | |
| 2006/0135963 A1 | 6/2006 | Kick | |
| 2006/0149193 A1 | 7/2006 | Hall | |
| 2006/0156875 A1 | 7/2006 | McRury | |
| 2006/0167416 A1 | 7/2006 | Mathis | |
| 2006/0178670 A1 | 8/2006 | Woloszko | |
| 2006/0189891 A1 | 8/2006 | Waxman | |
| 2006/0258938 A1 | 11/2006 | Hoffman | |
| 2007/0016164 A1 | 1/2007 | Dudney | |
| 2007/0025874 A1 | 2/2007 | Ophardt | |
| 2007/0027443 A1 | 2/2007 | Rose | |
| 2007/0027534 A1 | 2/2007 | Bergheim | |
| 2007/0032906 A1 | 2/2007 | Sutherland | |
| 2007/0038112 A1 | 2/2007 | Taylor | |
| 2007/0106304 A1 | 5/2007 | Hammack | |
| 2007/0129680 A1 | 6/2007 | Hagg | |
| 2007/0135763 A1 | 6/2007 | Musbach | |
| 2007/0135803 A1 | 6/2007 | Belson | |
| 2007/0185474 A1 | 8/2007 | Nahen | |
| 2007/0208375 A1 | 9/2007 | Nishizawa | |
| 2007/0213668 A1 | 9/2007 | Spitz | |
| 2007/0230757 A1 | 10/2007 | Trachtenberg | |
| 2007/0239153 A1 | 10/2007 | Hodorek et al. | |
| 2007/0239178 A1 | 10/2007 | Weitzner | |
| 2007/0250111 A1 | 10/2007 | Lu | |
| 2007/0278195 A1 | 12/2007 | Richerzhagen | |
| 2007/0299427 A1 | 12/2007 | Yeung | |
| 2008/0004603 A1 | 1/2008 | Larkin | |
| 2008/0015566 A1 | 1/2008 | Livneh | |
| 2008/0021440 A1 | 1/2008 | Solomon | |
| 2008/0032251 A1 | 2/2008 | Chou | |
| 2008/0033467 A1 | 2/2008 | Miyamoto | |
| 2008/0038124 A1 | 2/2008 | Kuehner | |
| 2008/0046122 A1 | 2/2008 | Manzo | |
| 2008/0065109 A1 | 3/2008 | Larkin | |
| 2008/0065111 A1 | 3/2008 | Blumenkranz | |
| 2008/0082091 A1 | 4/2008 | Rubtsov | |
| 2008/0097293 A1 | 4/2008 | Chin | |
| 2008/0097470 A1 | 4/2008 | Gruber | |
| 2008/0108934 A1 | 5/2008 | Berlin | |
| 2008/0114341 A1 | 5/2008 | Thyzel | |
| 2008/0125698 A1 | 5/2008 | Gerg | |
| 2008/0154258 A1 | 6/2008 | Chang | |
| 2008/0177285 A1 | 7/2008 | Brock | |
| 2008/0187101 A1 | 8/2008 | Gertner | |
| 2008/0188868 A1 | 8/2008 | Weitzner | |
| 2008/0196533 A1 | 8/2008 | Bergamasco | |
| 2008/0221602 A1 | 9/2008 | Kuehner | |
| 2008/0228104 A1 | 9/2008 | Uber | |
| 2008/0243157 A1 | 10/2008 | Klein | |
| 2008/0249526 A1 | 10/2008 | Knowlton | |
| 2008/0267468 A1 | 10/2008 | Geiger | |
| 2009/0012507 A1 | 1/2009 | Culbertson | |
| 2009/0018533 A1 | 1/2009 | Perkins | |
| 2009/0030446 A1 | 1/2009 | Measamer | |
| 2009/0036900 A1 | 2/2009 | Moll | |
| 2009/0043305 A1 | 2/2009 | Brodbeck | |
| 2009/0060764 A1 | 3/2009 | Mitzlaff | |
| 2009/0062602 A1 | 3/2009 | Rosenberg | |
| 2009/0082634 A1 | 3/2009 | Kathrani | |
| 2009/0088774 A1 | 4/2009 | Swarup | |
| 2009/0088775 A1 | 4/2009 | Swarup | |
| 2009/0105723 A1 | 4/2009 | Dillinger | |
| 2009/0131885 A1 | 5/2009 | Akahoshi | |
| 2009/0149712 A1 | 6/2009 | Fischer | |
| 2009/0157114 A1 | 6/2009 | Fischer | |
| 2009/0161827 A1 | 6/2009 | Gertner | |
| 2009/0171271 A1 | 7/2009 | Webster | |
| 2009/0227998 A1* | 9/2009 | Aljuri | A61B 17/32037 606/13 |
| 2009/0248041 A1 | 10/2009 | Williams | |
| 2009/0248043 A1 | 10/2009 | Tierney | |
| 2009/0254075 A1 | 10/2009 | Paz | |
| 2009/0264878 A1 | 10/2009 | Carmel | |
| 2009/0268015 A1 | 10/2009 | Scott | |
| 2009/0270760 A1 | 10/2009 | Leimbach | |
| 2009/0287045 A1 | 11/2009 | Mitelberg | |
| 2009/0287188 A1 | 11/2009 | Golden | |
| 2009/0299352 A1 | 12/2009 | Zerfas | |
| 2009/0312768 A1 | 12/2009 | Hawkins | |
| 2009/0326322 A1 | 12/2009 | Diolaiti | |
| 2010/0004642 A1 | 1/2010 | Lumpkin | |
| 2010/0010504 A1 | 1/2010 | Simaan | |
| 2010/0011900 A1 | 1/2010 | Burbank | |
| 2010/0011901 A1 | 1/2010 | Burbank | |
| 2010/0036294 A1 | 2/2010 | Mantell | |
| 2010/0073150 A1 | 3/2010 | Olson | |
| 2010/0076269 A1 | 3/2010 | Makower | |
| 2010/0082017 A1 | 4/2010 | Zickler | |
| 2010/0114115 A1 | 5/2010 | Schlesinger | |
| 2010/0145254 A1 | 6/2010 | Shadduck | |

(56) References Cited

U.S. PATENT DOCUMENTS

| | | |
|---|---|---|
| 2010/0179522 A1 | 7/2010 | Companion |
| 2010/0179632 A1 | 7/2010 | Bruszewski |
| 2010/0204605 A1 | 8/2010 | Blakley |
| 2010/0204646 A1 | 8/2010 | Plicchi |
| 2010/0217235 A1 | 8/2010 | Thorstenson |
| 2010/0225209 A1 | 9/2010 | Goldberg |
| 2010/0228191 A1 | 9/2010 | Alvarez |
| 2010/0228249 A1 | 9/2010 | Mohr |
| 2010/0268211 A1 | 10/2010 | Manwaring |
| 2010/0280320 A1 | 11/2010 | Alvarez |
| 2010/0280525 A1 | 11/2010 | Alvarez |
| 2010/0312141 A1 | 12/2010 | Keast |
| 2010/0333858 A1 | 12/2010 | Simaan |
| 2011/0009779 A1 | 1/2011 | Romano |
| 2011/0015483 A1 | 1/2011 | Barbagli |
| 2011/0015648 A1 | 1/2011 | Alvarez |
| 2011/0018439 A1 | 1/2011 | Fabbri |
| 2011/0028887 A1 | 2/2011 | Fischer |
| 2011/0040404 A1 | 2/2011 | Diolaiti |
| 2011/0046441 A1 | 2/2011 | Wiltshire |
| 2011/0071541 A1 | 3/2011 | Prisco |
| 2011/0071543 A1 | 3/2011 | Prisco |
| 2011/0104800 A1 | 5/2011 | Kensy |
| 2011/0106102 A1 | 5/2011 | Balicki |
| 2011/0106146 A1 | 5/2011 | Jeong |
| 2011/0125165 A1 | 5/2011 | Simaan |
| 2011/0152880 A1 | 6/2011 | Alvarez |
| 2011/0160713 A1 | 6/2011 | Neuberger |
| 2011/0167611 A1 | 7/2011 | Williams |
| 2011/0184291 A1 | 7/2011 | Okamura |
| 2011/0184391 A1 | 7/2011 | Aljuri |
| 2011/0213362 A1 | 9/2011 | Cunningham |
| 2011/0224660 A1 | 9/2011 | Neuberger |
| 2011/0238064 A1 | 9/2011 | Williams |
| 2011/0245757 A1 | 10/2011 | Myntti |
| 2011/0251578 A1 | 10/2011 | Peyman |
| 2011/0257641 A1 | 10/2011 | Hastings |
| 2011/0276085 A1 | 11/2011 | Krzyzanowski |
| 2011/0306836 A1 | 12/2011 | Ohline |
| 2011/0313343 A1 | 12/2011 | Milutinovic |
| 2012/0046605 A1 | 2/2012 | Uchida |
| 2012/0069167 A1 | 3/2012 | Liu |
| 2012/0138586 A1 | 6/2012 | Webster |
| 2012/0157841 A1 | 6/2012 | Glaenzer |
| 2012/0209315 A1 | 8/2012 | Amat Girbau |
| 2012/0232342 A1 | 9/2012 | Reydel |
| 2012/0253277 A1 | 10/2012 | Tah |
| 2012/0253332 A1 | 10/2012 | Moll |
| 2012/0259320 A1 | 10/2012 | Loesel |
| 2012/0283747 A1 | 11/2012 | Popovic |
| 2012/0296318 A1 | 11/2012 | Wellhoefer |
| 2012/0296394 A1 | 11/2012 | Culbertson |
| 2013/0006144 A1 | 1/2013 | Clancy |
| 2013/0035537 A1 | 2/2013 | Wallace |
| 2013/0053877 A1 | 2/2013 | Benmaamer |
| 2013/0066136 A1 | 3/2013 | Palese |
| 2013/0085442 A1 | 4/2013 | Shtul |
| 2013/0085482 A1 | 4/2013 | Van Valen |
| 2013/0085484 A1 | 4/2013 | Van Valen |
| 2013/0085486 A1 | 4/2013 | Boutoussov |
| 2013/0096422 A1 | 4/2013 | Boctor |
| 2013/0096574 A1 | 4/2013 | Kang |
| 2013/0110042 A1 | 5/2013 | Humphreys |
| 2013/0110107 A1 | 5/2013 | Smith |
| 2013/0116716 A1 | 5/2013 | Bahls |
| 2013/0144116 A1 | 6/2013 | Cooper |
| 2013/0144274 A1 | 6/2013 | Stefanchik |
| 2013/0144395 A1 | 6/2013 | Stefanchik |
| 2013/0190796 A1 | 7/2013 | Tilson |
| 2013/0225997 A1 | 8/2013 | Dillard |
| 2013/0226161 A1 | 8/2013 | Hickenbotham |
| 2013/0253267 A1 | 9/2013 | Collins |
| 2013/0253484 A1 | 9/2013 | Aljuri |
| 2013/0253488 A1 | 9/2013 | Aljuri |
| 2013/0261540 A1 | 10/2013 | Crank |
| 2013/0267889 A1 | 10/2013 | Aljuri |
| 2013/0303876 A1 | 11/2013 | Gelfand |
| 2013/0310819 A1 | 11/2013 | Neuberger |
| 2013/0345686 A1 | 12/2013 | Brown |
| 2014/0005681 A1 | 1/2014 | Gee |
| 2014/0012276 A1 | 1/2014 | Alvarez |
| 2014/0039681 A1 | 2/2014 | Bowling |
| 2014/0046308 A1 | 2/2014 | Bischoff |
| 2014/0051985 A1 | 2/2014 | Fan |
| 2014/0058361 A1 | 2/2014 | Gordon |
| 2014/0058365 A1 | 2/2014 | Bille |
| 2014/0058404 A1 | 2/2014 | Hammack |
| 2014/0058428 A1 | 2/2014 | Christopher |
| 2014/0100445 A1 | 4/2014 | Stenzel |
| 2014/0142591 A1 | 5/2014 | Alvarez |
| 2014/0163318 A1 | 6/2014 | Swanstrom |
| 2014/0193833 A1 | 7/2014 | Srivastava |
| 2014/0194859 A1 | 7/2014 | Ianchulev |
| 2014/0194905 A1 | 7/2014 | Kappel |
| 2014/0243849 A1 | 8/2014 | Saglam |
| 2014/0275956 A1 | 9/2014 | Fan |
| 2014/0276594 A1 | 9/2014 | Tanner |
| 2014/0276723 A1 | 9/2014 | Parihar |
| 2014/0276956 A1 | 9/2014 | Crainich |
| 2014/0309649 A1 | 10/2014 | Alvarez |
| 2014/0309655 A1 | 10/2014 | Gal |
| 2014/0316203 A1 | 10/2014 | Carroux |
| 2014/0357984 A1 | 12/2014 | Wallace |
| 2014/0364870 A1 | 12/2014 | Alvarez |
| 2015/0025539 A1 | 1/2015 | Alvarez |
| 2015/0045777 A1 | 2/2015 | Aljuri |
| 2015/0051592 A1 | 2/2015 | Kintz |
| 2015/0057646 A1 | 2/2015 | Aljuri |
| 2015/0080879 A1 | 3/2015 | Trees |
| 2015/0088107 A1 | 3/2015 | Aljuri |
| 2015/0088110 A1 | 3/2015 | Aljuri |
| 2015/0119638 A1 | 4/2015 | Yu |
| 2015/0127045 A1 | 5/2015 | Prestel |
| 2015/0133960 A1 | 5/2015 | Lohmeier |
| 2015/0164522 A1 | 6/2015 | Budiman |
| 2015/0164594 A1 | 6/2015 | Romo |
| 2015/0164596 A1 | 6/2015 | Romo |
| 2015/0201917 A1 | 7/2015 | Snow |
| 2015/0202085 A1 | 7/2015 | Lemonis |
| 2015/0313666 A1 | 11/2015 | Aljuri |
| 2015/0314110 A1 | 11/2015 | Park |
| 2015/0335344 A1 | 11/2015 | Aljuri |
| 2015/0335480 A1 | 11/2015 | Alvarez |
| 2016/0001038 A1 | 1/2016 | Romo |
| 2016/0022289 A1 | 1/2016 | Wan |
| 2016/0022466 A1 | 1/2016 | Pedtke |
| 2016/0030073 A1 | 2/2016 | Isakov |
| 2016/0045208 A1 | 2/2016 | Ciulla |
| 2016/0051318 A1 | 2/2016 | Manzo |
| 2016/0066935 A1 | 3/2016 | Nguyen |
| 2016/0074059 A1 | 3/2016 | Aljuri |
| 2016/0143778 A1 | 5/2016 | Aljuri |
| 2016/0151122 A1 | 6/2016 | Alvarez |
| 2016/0158490 A1 | 6/2016 | Leeflang |
| 2016/0183841 A1 | 6/2016 | Duindam |
| 2016/0199984 A1 | 7/2016 | Lohmeier |
| 2016/0228141 A1 | 8/2016 | Aljuri |
| 2016/0235495 A1 | 8/2016 | Wallace |
| 2016/0249932 A1 | 9/2016 | Rogers |
| 2016/0270865 A1 | 9/2016 | Landey |
| 2016/0279394 A1 | 9/2016 | Moll |
| 2016/0287279 A1 | 10/2016 | Bovay |
| 2016/0303743 A1 | 10/2016 | Rockrohr |
| 2016/0331358 A1 | 11/2016 | Gordon |
| 2016/0367324 A1 | 12/2016 | Sato |
| 2016/0374541 A1 | 12/2016 | Agrawal |
| 2017/0007337 A1 | 1/2017 | Dan |
| 2017/0049471 A1 | 2/2017 | Gaffney |
| 2017/0065227 A1 | 3/2017 | Marrs |
| 2017/0095234 A1 | 4/2017 | Prisco |
| 2017/0095295 A1 | 4/2017 | Overmyer |
| 2017/0100199 A1 | 4/2017 | Yu |
| 2017/0119413 A1 | 5/2017 | Romo |
| 2017/0119481 A1 | 5/2017 | Romo |

(56) References Cited

U.S. PATENT DOCUMENTS

| | | |
|---|---|---|
| 2017/0135706 A1 | 5/2017 | Frey |
| 2017/0151416 A1 | 6/2017 | Kutikov |
| 2017/0165011 A1 | 6/2017 | Bovay |
| 2017/0172553 A1 | 6/2017 | Chaplin |
| 2017/0172673 A1 | 6/2017 | Yu |
| 2017/0202627 A1 | 7/2017 | Sramek |
| 2017/0209073 A1 | 7/2017 | Sramek |
| 2017/0245878 A1 | 8/2017 | Aljuri |
| 2017/0252096 A1 | 9/2017 | Felder |
| 2017/0265923 A1 | 9/2017 | Privitera |
| 2017/0290631 A1 | 10/2017 | Lee |
| 2017/0319289 A1 | 11/2017 | Neff |
| 2017/0333679 A1 | 11/2017 | Jiang |
| 2017/0340396 A1 | 11/2017 | Romo |
| 2017/0367782 A1 | 12/2017 | Schuh |
| 2018/0000563 A1 | 1/2018 | Shanjani |
| 2018/0025666 A1 | 1/2018 | Ho |
| 2018/0049824 A1 | 2/2018 | Harris |
| 2018/0177383 A1 | 6/2018 | Noonan |
| 2018/0177556 A1 | 6/2018 | Noonan |
| 2018/0193049 A1 | 7/2018 | Heck |
| 2018/0214011 A1 | 8/2018 | Graetzel |
| 2018/0221038 A1 | 8/2018 | Noonan |
| 2018/0221039 A1 | 8/2018 | Shah |
| 2018/0250083 A1 | 9/2018 | Schuh |
| 2018/0271616 A1 | 9/2018 | Schuh |
| 2018/0279852 A1 | 10/2018 | Rafii-Tari |
| 2018/0280660 A1 | 10/2018 | Landey |
| 2018/0289243 A1 | 10/2018 | Landey |
| 2018/0289431 A1 | 10/2018 | Draper |
| 2018/0296285 A1 | 10/2018 | Simi |
| 2018/0325499 A1 | 11/2018 | Landey |
| 2018/0333044 A1 | 11/2018 | Jenkins |
| 2018/0360435 A1 | 12/2018 | Romo |
| 2019/0000559 A1 | 1/2019 | Berman |
| 2019/0000560 A1 | 1/2019 | Berman |
| 2019/0000566 A1 | 1/2019 | Graetzel |
| 2019/0000568 A1 | 1/2019 | Connolly |
| 2019/0000576 A1 | 1/2019 | Mintz |
| 2019/0083183 A1 | 3/2019 | Moll |
| 2019/0099231 A1 | 4/2019 | Bruehwiler |
| 2019/0105776 A1 | 4/2019 | Ho |
| 2019/0105785 A1 | 4/2019 | Meyer |
| 2019/0107454 A1 | 4/2019 | Lin |
| 2019/0110839 A1 | 4/2019 | Rafii-Tari |
| 2019/0110843 A1 | 4/2019 | Ummalaneni |
| 2019/0151148 A1 | 5/2019 | Alvarez |
| 2019/0167366 A1 | 6/2019 | Ummalaneni |
| 2019/0175009 A1 | 6/2019 | Mintz |
| 2019/0175062 A1 | 6/2019 | Rafii-Tari |
| 2019/0175287 A1 | 6/2019 | Hill |
| 2019/0175799 A1 | 6/2019 | Hsu |
| 2019/0183585 A1 | 6/2019 | Rafii-Tari |
| 2019/0183587 A1 | 6/2019 | Rafii-Tari |
| 2019/0216548 A1 | 7/2019 | Ummalaneni |
| 2019/0216576 A1 | 7/2019 | Eyre |
| 2019/0223974 A1 | 7/2019 | Romo |
| 2019/0228525 A1 | 7/2019 | Mintz |
| 2019/0231426 A1 | 8/2019 | Aljuri |
| 2019/0239890 A1 | 8/2019 | Stokes |
| 2019/0246882 A1 | 8/2019 | Graetzel |
| 2019/0247071 A1 | 8/2019 | Aljuri |
| 2019/0262086 A1 | 8/2019 | Connolly |
| 2019/0269468 A1 | 9/2019 | Hsu |
| 2019/0274764 A1 | 9/2019 | Romo |
| 2019/0290109 A1 | 9/2019 | Agrawal |
| 2019/0298160 A1 | 10/2019 | Ummalaneni |
| 2019/0298460 A1 | 10/2019 | Al-Jadda |
| 2019/0298465 A1 | 10/2019 | Chin |
| 2019/0314616 A1 | 10/2019 | Moll |
| 2019/0328213 A1 | 10/2019 | Landey |
| 2019/0336238 A1 | 11/2019 | Yu |
| 2019/0365209 A1 | 12/2019 | Ye |
| 2019/0365479 A1 | 12/2019 | Rafii-Tari |
| 2019/0365486 A1 | 12/2019 | Srinivasan |
| 2019/0374297 A1 | 12/2019 | Wallace |
| 2019/0375383 A1 | 12/2019 | Auer |
| 2019/0380787 A1 | 12/2019 | Ye |
| 2019/0380797 A1 | 12/2019 | Yu |
| 2020/0000530 A1 | 1/2020 | Defonzo |
| 2020/0000533 A1 | 1/2020 | Schuh |
| 2020/0022767 A1 | 1/2020 | Hill |
| 2020/0039086 A1 | 2/2020 | Meyer |
| 2020/0046434 A1 | 2/2020 | Graetzel |
| 2020/0054408 A1 | 2/2020 | Schuh |
| 2020/0060516 A1 | 2/2020 | Baez, Jr. |
| 2020/0093549 A1 | 3/2020 | Chin |
| 2020/0093554 A1 | 3/2020 | Schuh |
| 2020/0100845 A1 | 4/2020 | Julian |
| 2020/0100853 A1 | 4/2020 | Ho |
| 2020/0100855 A1 | 4/2020 | Leparmentier |
| 2020/0101264 A1 | 4/2020 | Jiang |
| 2020/0107894 A1 | 4/2020 | Wallace |
| 2020/0121502 A1 | 4/2020 | Kintz |
| 2020/0146769 A1 | 5/2020 | Eyre |
| 2020/0163726 A1 | 5/2020 | Tanner |

FOREIGN PATENT DOCUMENTS

| | | |
|---|---|---|
| CN | 1725992 A | 1/2006 |
| CN | 101108138 A | 1/2008 |
| CN | 101394877 A | 3/2009 |
| CN | 101443069 A | 5/2009 |
| CN | 100515347 C | 7/2009 |
| CN | 101902950 A | 12/2010 |
| CN | 102238921 A | 11/2011 |
| CN | 102724939 A | 10/2012 |
| CN | 103298414 A | 9/2013 |
| CN | 205729413 U | 11/2016 |
| DE | 9200447 U1 | 5/1992 |
| EP | 0598984 A1 | 6/1994 |
| EP | 0657150 | 6/1995 |
| EP | 0821916 A2 | 2/1998 |
| EP | 1075853 A2 | 2/2001 |
| EP | 1321106 A1 | 6/2003 |
| EP | 1683495 | 7/2006 |
| EP | 1849423 A2 | 10/2007 |
| EP | 3188667 A1 | 7/2017 |
| JP | S61263444 A | 11/1986 |
| JP | S62117548 A | 5/1987 |
| JP | 05076540 | 3/1993 |
| JP | 6509241 A | 10/1994 |
| JP | H06509241 A | 10/1994 |
| JP | 3476878 B2 | 5/1995 |
| JP | H07136173 A | 5/1995 |
| JP | H09505759 A | 6/1997 |
| JP | H09224951 A | 9/1997 |
| JP | H11332880 A | 12/1999 |
| JP | 2000511089 | 8/2000 |
| JP | 2001046528 A | 2/2001 |
| JP | 2001509038 A | 7/2001 |
| JP | 2001512358 A | 8/2001 |
| JP | 3349716 | 11/2002 |
| JP | 2003000713 A | 1/2003 |
| JP | 2003506131 A | 2/2003 |
| JP | 2004105707 A | 4/2004 |
| JP | 2004530477 A | 10/2004 |
| JP | 2005523741 A | 8/2005 |
| JP | 2005270464 A | 10/2005 |
| JP | 2006122307 A | 5/2006 |
| JP | 2006271691 A | 10/2006 |
| JP | 2007020837 A | 2/2007 |
| JP | 2007209465 A | 8/2007 |
| JP | 2009502304 A | 1/2009 |
| JP | 2009518134 A | 5/2009 |
| JP | 2010514541 A | 5/2010 |
| JP | 2010520801 A | 6/2010 |
| JP | 2011067330 | 4/2011 |
| JP | 2011514211 A | 5/2011 |
| WO | 9818388 A1 | 5/1988 |
| WO | 9004363 A1 | 5/1990 |
| WO | 9210142 A1 | 6/1992 |
| WO | 9312446 A1 | 6/1993 |
| WO | 9315664 A1 | 8/1993 |

(56) References Cited

FOREIGN PATENT DOCUMENTS

| | | |
|---|---|---|
| WO | 9426185 | 11/1994 |
| WO | 9639952 | 12/1996 |
| WO | 9640476 A1 | 12/1996 |
| WO | 9729803 A1 | 8/1997 |
| WO | 9956907 A1 | 11/1999 |
| WO | 0059394 A1 | 10/2000 |
| WO | 0149195 A1 | 7/2001 |
| WO | 02091935 A1 | 11/2002 |
| WO | 03088833 A1 | 10/2003 |
| WO | 03096871 A1 | 11/2003 |
| WO | 2004028592 A1 | 4/2004 |
| WO | 2004080529 A2 | 9/2004 |
| WO | 2004105849 A1 | 12/2004 |
| WO | 2006066160 A1 | 6/2006 |
| WO | 2007011302 A1 | 1/2007 |
| WO | 2007114917 | 10/2007 |
| WO | 2007114917 A2 | 10/2007 |
| WO | 2008083407 A1 | 7/2008 |
| WO | 2009111736 A1 | 9/2009 |
| WO | 2009152613 A1 | 12/2009 |
| WO | 2010054237 | 5/2010 |
| WO | 2010144419 A2 | 12/2010 |
| WO | 2011097505 A1 | 8/2011 |
| WO | 2011100753 A2 | 8/2011 |
| WO | 2011141775 A1 | 11/2011 |
| WO | 2011161218 A1 | 12/2011 |
| WO | 2013009576 A1 | 1/2013 |
| WO | 2013107468 A1 | 7/2013 |
| WO | 2013130895 A1 | 9/2013 |
| WO | 2014127242 | 8/2014 |
| WO | 2014127242 A2 | 8/2014 |
| WO | 2015200538 A1 | 12/2015 |
| WO | 2016004071 A1 | 1/2016 |
| WO | 2016037132 A1 | 3/2016 |
| WO | 2017114855 A1 | 7/2017 |
| WO | 2018069679 A1 | 4/2018 |

OTHER PUBLICATIONS

Balicki, et al., "Single fiber optical coherence tomography microsurgical instruments for computer and robot-assisted retinal surgery". Medical Image Computing and Computer-Assisted Intervention. G.-Z. Yang et al. (Eds.): MICCAI 2009, Part I, LNCS 5761, pp. 108-115, 2009.
Botto et al., "Electrovaporization of the Prostate with the Gyrus Device," J. Endourol. (Apr. 2001) 15(3):313-316.
Ehlers, et al., "Integration of a spectral domain optical coherence tomography system into a surgical microscope for intraoperative imaging." Investigative Ophthalmology and Visual Science (2011); 52(6): 3153-3159.
EP09718273.7 Office Action dated Apr. 12, 2018.
European office action dated Aug. 20, 2015 for EP Application No. 11740445.9.
European search report and opinion dated Feb. 5, 2014 for EP Application No. 11740445.9.
European search report and opinion dated Jun. 18, 2012 for EP Application No. 08705642.0.
European search report and opinion dated Nov. 7, 2011 for EP Application No. 09718273.7.
European search report and opinion dated Nov. 7, 2014 for EP Application No. 14181197.6.
European search report and opinion dated Sep. 11, 2015 for EP Application No. 13754453.2.
European Search Report dated Jan. 13, 2017 for EP Application No. 13754453.2.
Extended European search report and opinion dated Jan. 25, 2016 for EP Application No. 13754453.2.
Extended European Search Report dated July 2, 2015 for EP Application No. 12856685.8, 6 pages.
Hillegersberg et al., "Water-jet-cooled Nd:YAG laser coagulation: selective destruction of rat liver metastases," Lasers Surg Med. 1991; 11(5):445-454. [Abstract Only].
International Preliminary Report on Patentability dated Sep. 2, 2014 for PCT/US2013/028441, 11 pages.
International Preliminary Report on Patentability dated Sep. 7, 2010 for PCT/US2009/036390, 9 pages.
International Search Report and Written Opinion dated Jan. 27, 2015 for PCT Application No. PCT/US2014/062284, 7 pages.
International Search Report and Written Opinion dated Jun. 16, 2014 for PCT/US2014/022424, 7 pages.
International Search Report and Written Opinion dated Jun. 27, 2013 for PCT/US2013/028441, 14 pages.
International search report and written opinion dated Mar. 10, 2015 for PCT Application No. US2014/054412.
International Search Report and Written Opinion dated Mar. 29, 2013 for PCT/US2012/069540, 7 pages.
International search report and written opinion dated May 21, 2008 for PCT/US2008/050051.
International Search Report and Written Opinion dated Nov. 7, 2014 in PCT/US2014/041990, 7 pages.
International Search Report and Written Opinion for International Application No. PCT/US2011/023781, 12 pages (dated Mar. 31, 2011).
International Search Report and Written Opinion of International Application No. PCT/US08/50051, 10 pages (dated May 21, 2008).
International Search Report for International Application No. PCT/US2009/036390, 3 pages (dated Apr. 24, 2009).
Jian, et al. The Development of the Water Jet Scalpel With Air Pressure. Trans. ASME (Jun. 2001) 123(2):246-248.
Nishimura, et al., "Similarity Law on Shedding Frequency of Cavitation Cloud Induced by a Cavitating Jet". Journal of Fluid Science and Technology (2012); vol. 7, No. 3, pp. 405-420.
Non-Final Office Action dated Jan. 26, 2018 for U.S. Appl. No. 14/952,840.
Notice of Allowance dated Apr. 19, 2016 for U.S. Appl. No. 14/334,247.
Notice of allowance dated Aug. 23, 2016 for U.S. Appl. No. 14/540,331.
Notice of Allowance dated Jan. 9, 2019 for U.S. Appl. No. 14/952,840.
Notice of allowance dated Jul. 29, 2016 for U.S. Appl. No. 14/540,331.
Notice of allowance dated Jul. 7, 2014 for U.S. Appl. No. 12/399,585.
Notice of Allowance dated Mar. 1, 2017 for U.S. Appl. No. 14/540,310.
Notice of allowance dated Mar. 11, 2016 for U.S. Appl. No. 14/334,247.
Notice of allowance dated Mar. 29, 2016 for U.S. Appl. No. 13/790,144.
Notice of Allowance dated May 6, 2016 for U.S. Appl. No. 14/334,247.
Notice of Allowance dated Oct. 28, 2010 for U.S. Appl. No. 11/968,445.
Notice of allowance dated Sep. 15, 2015 for U.S. Appl. No. 12/700,568.
Notice of Allowance dated Sep. 21, 2016 for U.S. Appl. No. 14/540,331.
Notice of allowance dated Sep. 22, 2015 for U.S. Appl. No. 13/790,218.
Notice of allowance dated Sep. 4, 2015 for U.S. Appl. No. 13/792,780.
Notice of Allowance dated Sep. 6, 2018 for U.S. Appl. No. 14/952,840.
Office action dated Aug. 1, 2012 for U.S. Appl. No. 12/399,585.
Office action dated Aug. 18, 2016 for U.S. Appl. No. 14/540,310.
Office action dated Dec. 9, 2015 for U.S. Appl. No. 14/540,331.
Office action dated Feb. 26, 2015 for U.S. Appl. No. 13/792,780.
Office action dated Jan. 20, 2010 for U.S. Appl. No. 11/968,445.
Office action dated Jan. 31, 2013 for U.S. Appl. No. 12/399,585.
Office action dated Jan. 5, 2015 for U.S. Appl. No. 13/790,144.
Office Action dated Jan. 9, 2017 for U.S. Appl. No. 14/952,840.
Office Action dated Jul. 14, 2017 for U.S. Appl. No. 14/952,840.
Office action dated Jul. 28, 2014 for U.S. Appl. No. 12/700,568.
Office action dated Mar. 12, 2015 for U.S. Appl. No. 13/790,218.
Office action dated Mar. 17, 2015 for U.S. Appl. No. 12/700,568.
Office action dated Mar. 25, 2016 for U.S. Appl. No. 14/540,310.
Office action dated Mar. 5, 2009 for U.S. Appl. No. 11/968,445.
Office action dated Nov. 5, 2015 for U.S. Appl. No. 14/334,247.

(56) References Cited

OTHER PUBLICATIONS

Office action dated Nov. 6, 2013 for U.S. Appl. No. 12/399,585.
Office action dated Oct. 5, 2009 for U.S. Appl. No. 11/968,445.
Office action dated Sep. 12, 2014 for U.S. Appl. No. 13/790,218.
Office action dated Sep. 12, 2014 for U.S. Appl. No. 13/792,780.
Office action dated Sep. 15, 2015 for U.S. Appl. No. 13/790,144.
Office action dated Sep. 30, 2010 for U.S. Appl. No. 11/968,445.
Pitcher, et al., "Robotic Eye Surgery: Past, Present, and Future". Journal of Computer Science and Systems Biology (2012); S3, 4 pages.
Prajapati, et al., Pluripotent Stem Cell within the Prostate could be Responsible for Benign Prostate Hyperplasia in Human, J Stem Cell Res Ther2014, 4:1.
Prajapati, et al., Prostate Stem Cells in the Development of Benign Prostate Hyperplasia and Prostate Cancer: Emerging Role and Concepts, Biomed Res Inf 2013; 2013:107954.
Richerzhagen et al., "Water Jet Guided Laser Cutting: a Powerful Hybrid Technology for Fine Cutting and Grooving," Proceedings of the 2004 Advanced Laser Applications Conference and Exposition, Ann Arbor, Michigan, Sep. 20-22, 2004, ALAC 2004, 2:175-182; retrieved from the Internet <http://www.synova.ch/pdf/ALAC04.pdf>.
Sander et al., "The waterjet-guided Nd:YAG laser in the treatment of gastroduodenal ulcer with a visible vessel. A randomized controlled and prospective study," Endoscopy. Sep. 1989; 21(5):217-220. [Abstract Only].
Sander et al., "Waterjet guided Nd:YAG laser coagulation—its application in the field of gastroenterology," Endosc Surg Allied Technol. Aug. 1993; 1(4):233-238. [Abstract Only].
Stalder et al., "Repetitive Plasma Discharges in Saline Solutions," Appl. Phys. Lett. (Dec. 2001), 79(27):4503-4505.
Stoyanov, Daniel, "Surgical Vision", Annals of Biomedical Engineering (Oct. 20, 2011); 40(2):332-345. Abstract Only.
Verdaasdonk, et al., "Effect of microsecond pulse length and tip shape on explosive bubble formation of 2.78 μm Er, Cr;YSGG and 2.94 μm Er:YAG laser". Proceedings of SPIE, Jan. 23, 2012, vol. 8221-12, 1 page.
Woloszko et al., "Plasma Characteristics of Repetitively-Pulsed Electrical Discharges in Saline Solutions Used for Surgical Procedures," (2002) IEEE Trans. Plasma Sci. 30(3):1376-1383.
Wright, et al., "Cavitation of a submerged jet." Exp Fluids (2013); 54:1541, 21 pages.
Office Action for U.S. Appl. No. 16/894,130 dated Feb. 25, 2021, 12 pages.
Office Action (Non-Final) for U.S. Appl. No. 17/125,586, 14 pages (dated May 14, 2021).

\* cited by examiner

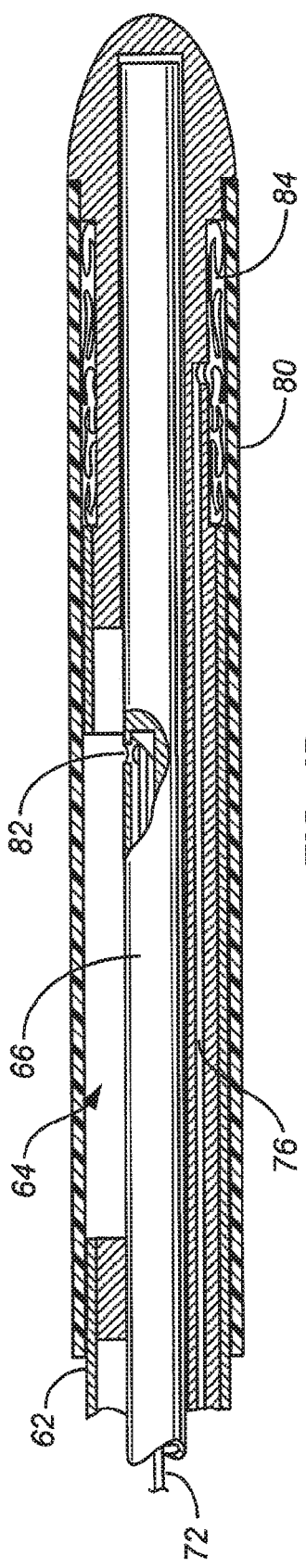
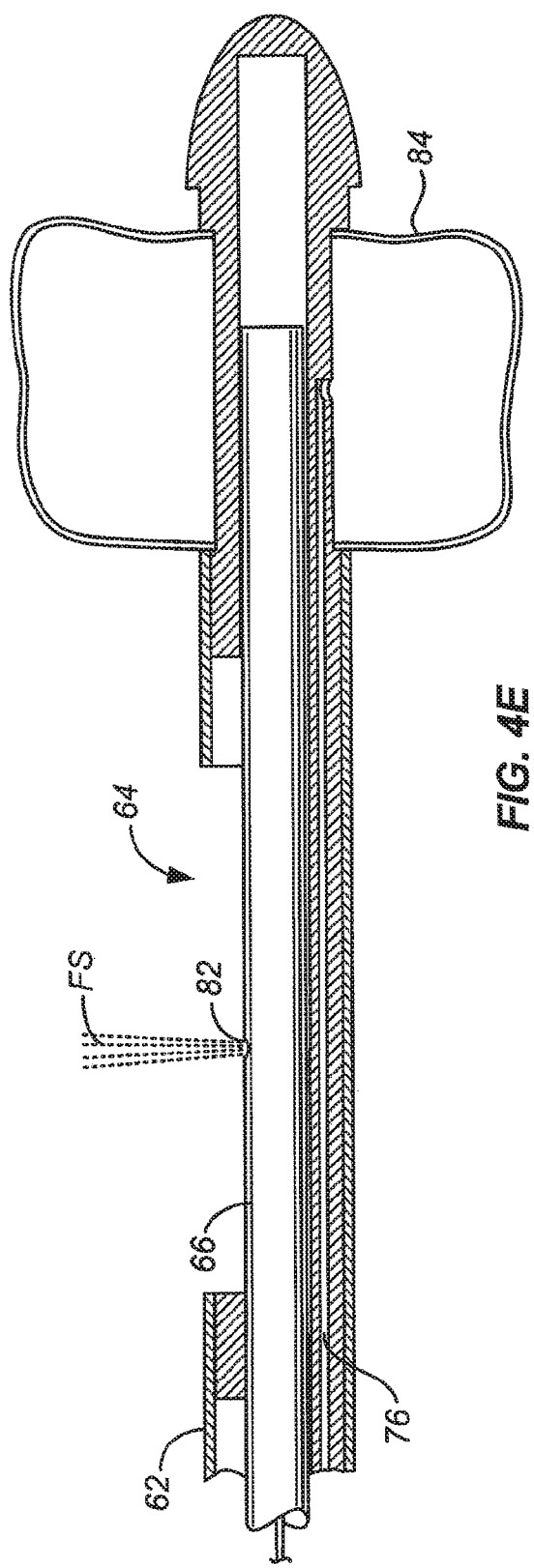
FIG. 4D
FIG. 4E

ABLATION WITH ENERGY CARRIED IN FLUID STREAM

CROSS-REFERENCES TO RELATED APPLICATIONS

This application is a continuation of U.S. patent application Ser. No. 16/382,631, filed Apr. 12, 2019, now U.S. Pat. No. 11,033,330, issued Jun. 15, 2021, which is a continuation of U.S. patent application Ser. No. 14/336,606, filed Jul. 21, 2014, now U.S. Pat. No. 10,342,615, issued Jul. 9, 2019, which is a continuation of U.S. patent application Ser. No. 12/399,585, filed Mar. 6, 2009, now U.S. Pat. No. 8,814,921, issued Aug. 26, 2014, which application claims the benefit under 35 U.S.C. § 119(e) of U.S. Provisional Application No. 61/097,497, filed Sep. 16, 2008, and of U.S. Provisional Application No. 61/034,412, filed Mar. 6, 2008, all of which are incorporated herein by reference in their entirety. The subject matter of this application is related to U.S. patent application Ser. No. 11/968,445, filed Jan. 2, 2008, now U.S. Pat. No. 7,882,841, issued Feb. 8, 2011, which claims the benefit under 35 U.S.C. § 119(e) of U.S. Provisional Application No. 60/883,097, filed Jan. 2, 2007, the full disclosures of which are incorporated herein by reference.

BACKGROUND OF THE INVENTION

Field of the Invention

The present invention relates generally to medical methods and devices. In particular, the present invention relates to methods and devices for applying energy to ablate, cut, drill, or otherwise modify soft or hard tissues.

Both water jet technology and laser technology have been proposed for various tissue cutting and modification protocols. While each of these approaches has achieved commercial success, neither is ideally suited for all tissue modification protocols. For example, water jet or stream cutting alone does not cauterize tissue and therefore cannot prevent excessive bleeding. Furthermore, it can require very high-pressure water delivery systems which can be difficult to control. Similarly, the use of lasers for modifying tissue can require very high energies, which can only be generated with large high power and expensive laser equipment. While laser technology can be effectively applied to cauterize tissue and stop bleeding, an extensive tissue zone of thermal damage is unavoidable. The consequences are the formation of edema and swelling of the treated tissue. With prostate tissue for example, tissue edema and swelling may result with the patient going into urinary retention requiring catheterization. Thus, improved energy-based methods and devices for ablating, cutting, drilling, and otherwise modifying tissues, would be desirable.

A number of medical conditions affect the male urethra causing a variety of symptoms including painful or difficult urination, a swollen prostate, blood in the urine, lower back pain, and the like. Some of these conditions, such as prostatitis, are bacterial infections which can be treated with antibiotics and other drugs. Other conditions, however, such as benign prostatic hyperplasia (BPH) and prostatic carcinoma, result in enlargement of the prostate and obstruction of the urethra, sometimes leading to complete loss of bladder function.

Both BPH and prostatic cancer require treatments which remove, resect, or shrink tissue in the prostate surrounding the urethra. Common treatments include transurethral resection of the prostate (TURP) where a resectoscope is placed in the urethra and used to remove excess prostatic tissue. Another procedure, referred to as transurethral incision of the prostate (TUIP), relies on cutting muscle adjacent to the prostate to relax the bladder opening to relieve difficulty in urination. More recently, a procedure referred to as transurethral needle ablation (TUNA) has been introduced where a needle is advanced through the urethra into the prostate and used to deliver energy, such as microwave, radiofrequency, or ultrasound energy, to shrink the size of the prostate, again relieving pressure on the urethra. Laser resection or ablation using transurethral optical fibers also finds use.

One minimally invasive laser resection protocol is photoselective vaporization of the prostate (PVP) where a laser beam with output powers ranging from 60 to 120 W is directed from the urethra against prostatic tissue to achieve irradiance (power density) levels over a certain volumetric power density, referred to as a vaporization threshold, below which tissue coagulation rather than vaporization occurs. As the irradiance level increases above the vaporization threshold, tissue vaporization increases and coagulation decreases. Lasers, even those having the highest possible beam quality, produce divergent beams. Therefore, the laser spot size enlarges with increasing probe distance from the tissue, and the power density decreases. reducing the rate of vaporization. Hence, in order to maximize the rate of tissue vaporization and thereby limit the extent of the zone of thermal damage characterized by tissue coagulation left after the procedure, the physician must steadily hold the fiber a fixed distance (e.g., 1-2 mm) away from the tissue and slowly scan the beam over the target tissue without varying the distance. Clearly, the effectiveness and duration of this procedure is highly dependent on the skill of the treating physician and the use of a high-power laser.

While generally successful, none of these methods are adequate to treat all patients and all conditions. In particular, patients having severe tissue intrusion into the urethral lumen resulting from BPH or prostatic cancer are difficult to treat with minimally invasive protocols which rely on tissue shrinkage rather than resection. Additionally, those treatments which resect tissue often cause substantial bleeding which can be difficult to staunch. Thus, many of these patients will eventually require conventional surgical resection or follow-up procedures to stop bleeding.

For these reasons, it would be desirable to provide alternative and improved tissue-modifying systems which rely on the application of energy from one or more sources to the tissue. In particular, it would be desirable to provide minimally invasive methods and devices which provide for enlarging the luminal area and/or volumetric resection of tissue surrounding the urethra. It would be particularly desirable if such methods and devices were transurethrally introduced and provided for rapid removal or destruction of such tissues surrounding the urethra where the removal or destruction products can be removed from the lumen to relieve pressure on the urethra, even where large volumes of tissue are being removed. It would be particularly desirable if the methods and devices allowed for controllable tissue resection and/or ablation depth from very shallow depths to several millimeters or deeper. It would also be advantageous if the ablation could simultaneously cauterize treated tissue to limit bleeding. It would also be desirable if the depth of residual coagulated tissue that remains after tissue ablation were minimized or completely eliminated. It would be a further advantage if the use of a high-power laser were not required. It would be particularly beneficial if the methods and devices allowed for rapid and controlling tissue ablation or resection which is less dependent on skill of the treating physician. Methods and devices for performing such protocols should present minimal risk to the patient, should be relatively easy to perform by the treating physician, and should allow for alleviation of symptoms with minimal complications and side effects even in patients with severe disease. At least some of these objectives will be met by the inventions described below.

Description of the Background Art

The use of water or other fluid jets as waveguides for carrying a laser beam for cutting and other manufacturing operations is described in U.S. Patent Application No. 2007/0278195, published Canadian application 2,330436 A1, PCT publication WO 99/56907, and U.S. Pat. Nos. 7,163,875; 5,902,499; and 5,773,791. U.S. Patent Application No. 2007/0025874 describes the use of laser fluid jets for disinfecting hands. The use of lasers for cutting biological tissue is described in U.S. Patent Application No. 2002/0128637 and for ablating prostate tissue is described in U.S. Pat. Nos. 5,257,991; 5,514,669; and 6,986,764. Use of a transurethral endoscope for bipolar radiofrequency prostate vaporization is described in Boffo et al. (2001) *J. Endourol.* 15:313-316. Pressurized water streams for effecting surgical incisions are described in U.S. Pat. Nos. 7,122,017 and 5,620,414, and for drilling teeth are described in U.S. Pat. No. 7,326,054. U.S. Pat. Nos. 5,785,521 and 6,607,524 describe the use of laser energy to cause thermo-elastic failure and fracture of hard biological materials combined with water/air technology to cool and remove (or further fracture) the already fractured material and debris from the treatment site. Radiofrequency discharge in saline solutions to produce tissue-ablative plasmas is discussed in Woloszko et al. (2002) *IEEE Trans. Plasma Sci.* 30:1376-1383 and Staider et al. (2001) *Appl. Phys. Lett.* 79:4503-4505. Air/water jets for resecting tissue are described in Jian and Jiajun (2001) *Trans. ASME* 246-248. US2005/0288639 described a needle injector on a catheter based system which can be anchored in a urethra by a balloon in the bladder. U.S. Pat. Nos. 6,890,332; 6,821,275; and 6,413,256 each describe catheters for producing an RF plasma for tissue ablation. Other patents and published applications of interest include: U.S. Pat. Nos. 7,015,253; 6,953,461; 6,890,332, 6,821,275; 6,451,017; 6,413,256; 6,378,525; 6,296,639; 6,231,591; 6217,860; 6,200,573; 6,179,831; 6,142,991; 6,022,860; 5,994,362; 5,872,150; 5,861,002; 5,817,649; 5,770,603; 5,753,641; 5,672,171; 5,630,794; 5,562,703; 5,322,503; 5,116,615; 4,760,071; 4,636,505; 4,461,283; 4,386,080; 4,377,584; 4,239,776; 4,220,753; 4,097,578; 3,875,229; 3,847,988; US2002/0040220; US2001/0048942; WO 93/15664; and WO 92/10142.

BRIEF SUMMARY OF THE INVENTION

Methods, devices, and systems according to the present invention provide for delivery of coherent light and fluid energy to ablate, resect, drill, cut, or otherwise modify tissue. The tissues to be treated can be soft tissue, such as muscle, organ tissue, nerve tissue, cerebral tissue, skin tissue, glandular tissue or the like, or can be hard tissue, such as tooth, bone, cartilage, or the like. Particular treatments include ablation, such volumetric tissue ablation where volumes or regions of the tissue are vaporized, shrunk, necrosed or the like. The tissue modification can also be cutting where the tissue is severed into pieces or regions along a resection plane or can be drilling where a hole is formed into the tissue, such as drilling into a tooth, or the like.

The present invention is particularly intended for treating/modifying soft and hard biological tissue. Depending on the power levels, treatment times, and treatment patterns selected, the present invention can provide for tissue resection, e.g. cutting along a line of tissue; tissue volume reduction; tissue surface modification; and the like. A particular advantage of the present invention arises from the simultaneous delivery of both fluid energy (constant or pulsating) in the form of a pressurized liquid medium and coherent light energy which will be propagated with constant power density through the fluid medium by total internal reflection thereby eliminating the need of laser focus-distance control. Where the pressurized fluid medium is principally relied on for cutting or tissue ablation, the coherent light can be delivered at an energy level selected to provide cauterization, i.e. the staunching of bleeding which would otherwise occur as a result of the tissue resection or ablation. Alternatively, by using higher coherent light energy levels, the coherent light can work together with the pressurized fluid stream to achieve faster, deeper, or otherwise enhanced cutting, tissue volume reduction, or other tissue modifications with significantly diminished laser power requirements as compared to current treatments such as photoselective vaporization of the prostate (PVP).

Specific prostate treatments according to the present invention comprise positioning a coherent light and fluid energy source within the urethra and directing a fluid stream carrying the energy radially outwardly from the energy source toward the urethral wall within the prostate. The fluid stream will usually be moved relative to the urethra to remove a pre-defined volume of prostate tissue surrounding the urethral lumen in order to partially or fully relieve the compression and/or obstruction. In other embodiments, the treatments of the present invention may be combined with chemotherapy and other forms of drug delivery, as well as treatment with external X-ray and other radiation sources and administration of radiopharmaceuticals comprising therapeutic radioisotopes. For example, one or more drugs may be combined with the saline or other fluid which is being delivered. The combination liquid/coherent light delivery can be used to both resect tissue and wash the tissue away while leaving intra-prostatic blood vessels, capsule, and sphincter muscle undamaged.

Benefits of the high-pressure liquid/light energy source include reduced or no bleeding with reduced or no need for cauterization and decreased risk of perforating or otherwise damaging the capsule of sphincter muscles. Alternatively, the device which is used to position the fluid/light energy source can be utilized to separately deliver a desired chemotherapeutic or other drug (as just set forth), either before, during, or after energy treatment according to the present invention. While the present invention is specifically directed at transurethral treatment of the prostate, certain aspects of the invention may also find use in the treatment of other body lumens, organs, passages, tissues, and the like, such as the ureter, colon, esophagus, lung passages, bone marrow, and blood vessels.

Thus, in a first aspect of the present invention, methods for modifying tissue comprise generating a stream of a light transmissive fluid medium, such as saline, water, alcohol, liquefied $CO_2$ and other liquefied gases (gases which are liquids at the pressure and temperature of use), fluid containing drug compounds such as vasocontricting agents (to reduce bleeding) and/or anesthetic agents (to reduce pain)

and/or anti-inflammatory agents, antibiotics (to reduce infection), or the like. A source of coherent light, such as a laser, is coupled to the light transmissive medium through a waveguide or other optical coupler so that light is transmitted through said stream by total internal reflection. The fluid stream which carries the coherent light is then directed at target tissue, such as within the prostate.

While a particular advantage of the present invention is the simultaneous delivery of a pressurized fluid stream and laser or other optical energy, in some instances either the fluid stream or the optical energy may be delivered alone. For example, it may be desirable to deliver the fluid stream without optical energy to perform conventional water jet resection or volume reduction of tissue. After such water jet treatment, the optical energy can be added to cauterize and/or perform a procedure at a higher total energy. Optionally, the pressure, volume, flow velocity, temperature, or other characteristics of the fluid stream may be varied depending on whether optical energy is present, e.g., cauterization may be performed at lower pressures than tissue resection. In all cases the removed tissue and/or remaining tissue can be used for histological evaluation or other diagnostic procedures. It is a particular advantage that the removed tissue has not been vaporized or otherwise damaged to the extent it is with PVP and the subsequent analysis is impaired.

The liquid stream may be generated in a variety of ways, typically being delivered under pressure through a nozzle, where the nozzle typically has an area in the range from 0.0005 $mm^2$ to 5 $mm^2$, usually from 0.02 $mm^2$ to 0.2 $mm^2$, and the pressure is in the range from 10 psi to 1000 psi, typically from 50 Psi to 500 Psi. The light which is coupled into the light transmissive fluid will typically have a power level in the range from 10 mW to 40 W, typically from 100 mW to 10 W. Suitable laser sources include solid state lasers. For treating prostate tissue, the stream will be directed radially outward from a location in the urethra within the prostate.

Typically, prostate treatment will comprise positioning a probe within the urethra, directing the pressurized stream of light transmissive liquid medium radially outward from the probe to the prostate tissue surrounding the urethra. The coherent light is focused within the stream of liquid medium as the stream is directed at the prostate tissue. In this way, tissue volume reduction of the prostate may be efficiently carried out, while the coherent light can provide cauterization with minimal laser power to reduce the bleeding associated with the treatment.

In a second aspect of the present invention, a system for delivering laser or other coherent light energy to tissue comprises a tissue probe, a fluid nozzle on the probe, and a waveguide disposed within the probe. The tissue probe is suitable for introducing into solid tissue, tissue lumens, body cavities, or the like. In the exemplary embodiment, the tissue probe is suitable for transurethral introduction into the prostate so that a distal end of the probe is positioned within the prostate. A nozzle is provided for emitting a stream of light transmissive fluid, and a waveguide transmits coherent light into the fluid so that the fluid acts as a guide for further directing the coherent light to the tissue for treatment. Usually, the tissue probe will be adapted to be advanced through the urethra, but a wide variety of other specific designs would also be available for delivery into solid tissue, body lumens, or body cavities. Probes of the present invention typically have at least one central axial passage for delivering the light transmissive fluid to the nozzle, and the nozzle is typically disposed on the probe to deliver the fluid radially outwardly (laterally) under pressure.

In an exemplary embodiment, the probe comprises an outer tube having an axial lumen and an inner fluid delivery tube reciprocally mounted in the axial lumen. A central axial passage is disposed in the inner fluid delivery tube, and the waveguide is disposed in the central axial passage. In this way, the light transmissive fluid can be delivered through the central axial passage and diverted outwardly through the nozzle. The waveguide would be disposed to deliver coherent light through the central axial passage and to reflect or otherwise divert the light radially so that it is focused within the light transmissive fluid being delivered through the nozzle. By focusing the energy as it is emanating from the tissue probe, the light will be delivered through the fluid stream to assist in propagation.

In the specific embodiments, the distal end of the inner fluid delivery tube is disposed adjacent to a window in the outer tube. The inner tube may then be reciprocated and/or rotated relative to the outer tube so that the fluid stream and coherent light emanating from the inner fluid delivery tube may be delivered into tissue adjacent to or surrounding the outer tube through the window.

BRIEF DESCRIPTION OF THE DRAWINGS

FIGS. 4A-4E illustrate an alternative design for the tissue debulking device of the present invention, illustrating specific components and features for delivering fluids, inflating balloons, rotating and reciprocating the fluid and light delivery mechanism, and the like.

DETAILED DESCRIPTION OF THE INVENTION

Figure 1:
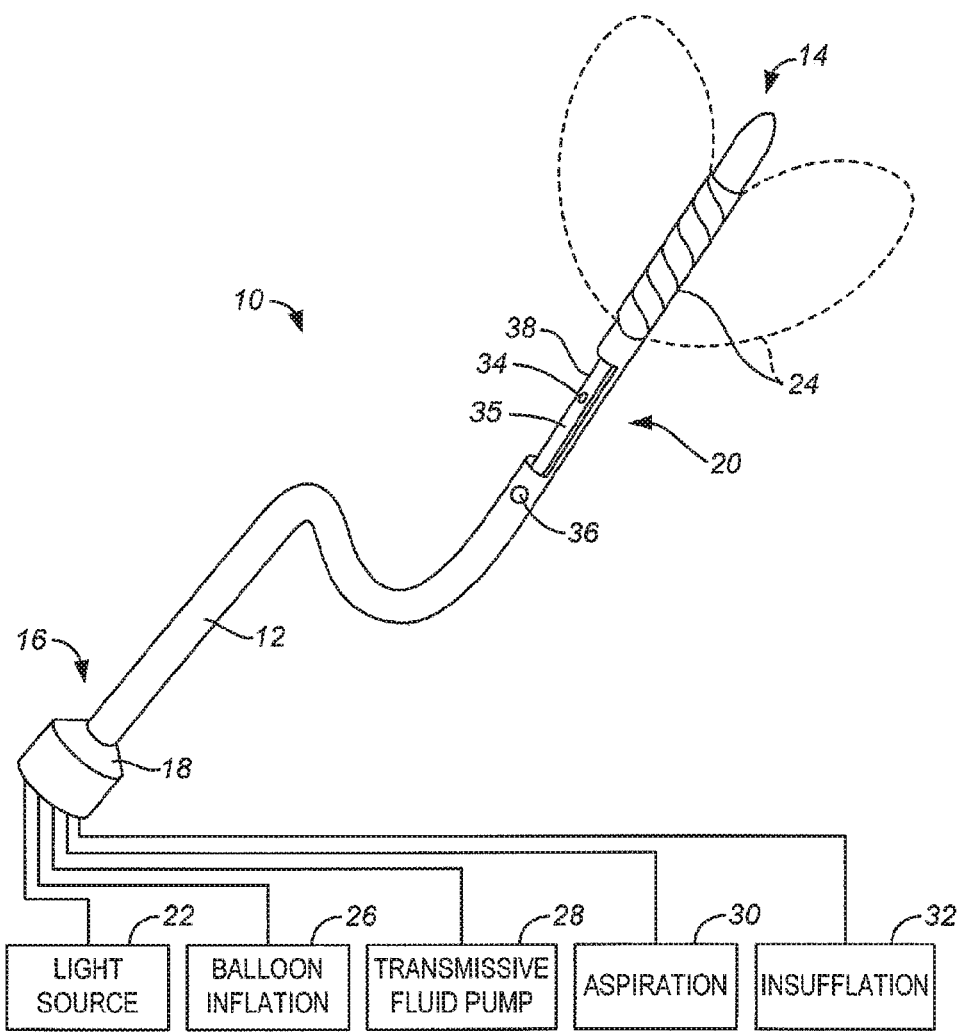
FIG. 1 is a schematic illustration of a device suitable for performing intraurethral prostatic tissue debulking in accordance with the principles of the present invention.

Referring to FIG. 1, an exemplary prostatic tissue debulking device 10 constructed in accordance with the principles of the present invention comprises a catheter assembly generally including a shaft 12 having a distal end 14 and a proximal end 16. The shaft 12 will typically be a polymeric extrusion including one, two, three, four, or more axial lumens extending from a hub 18 at the proximal end 16 to locations near the distal end 14. The shaft 12 will generally have a length in the range from 15 cm to 25 cm and a diameter in the range from 1 mm to 10 mm, usually from 4 mm to 8 mm. The shaft will have sufficient column strength so that it may be introduced upwardly through the male urethra, as described in more detail below.

The shaft will include a fluid/coherent light energy source 20 positioned near the distal end 14 of the shaft 12. The source 20, in turn, is connected to an external light source 22 and light transmissive fluid source 28. Distal to the energy source 20, an inflatable anchoring balloon 24 will be positioned at or very close to the distal end 14 of the shaft. The balloon will be connected through one of the axial lumens to a balloon inflation source 26 connected through the hub 18. In addition to the light source 22, fluid pump 28, and balloon inflation source 26, the hub will optionally further include connections for an aspiration (a vacuum) source 30, and/or an insufflation (pressurized $CO_2$ or other gas) source 32. In the exemplary embodiment, the fluid pump 28 can be connected through an axial lumen (not shown) to one or more port(s) 34 on an inner fluid delivery tube 35. The aspiration source 30 can be connected to a window or opening 38, usually positioned proximally of the energy source 20, while the insufflation source 32 can be connected to a port 36 formed in the wall of shaft 12. The energy will be directed through the window 38 as described in more detail below.

Figure 2:
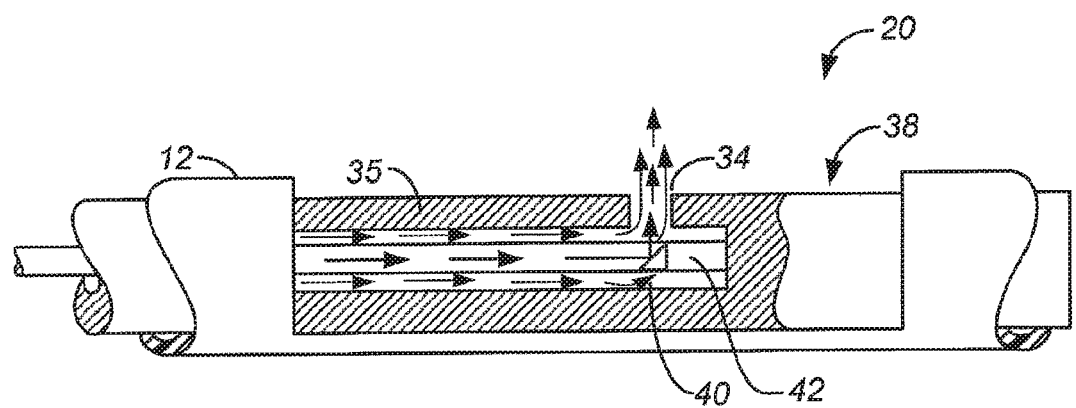
FIG. 2 is a detailed illustration of the pressurized fluid/coherent light delivery mechanism used in the device of FIG. 1.

Referring now to FIG. 2, the fluid/coherent light energy source 20 is defined by window 38 in the wall of shaft 12. The inner fluid delivery tube 35 is reciprocatably and rotatably mounted within a central lumen of the shaft 12 so that the port 34 may be rotated and/or axially advanced or retracted within the window relative to the shaft. The inner fluid delivery tube 35 has a central passage 40 which is attachable to the transmissive fluid pump 28 through the hub 18 to carry the transmissive fluid under pressure and emit a fluid or jet stream through the port 34 in a lateral direction. An optical waveguide 42 is also positioned within the central passage 40 of the inner fluid delivery tube 35.

Figure 2A:
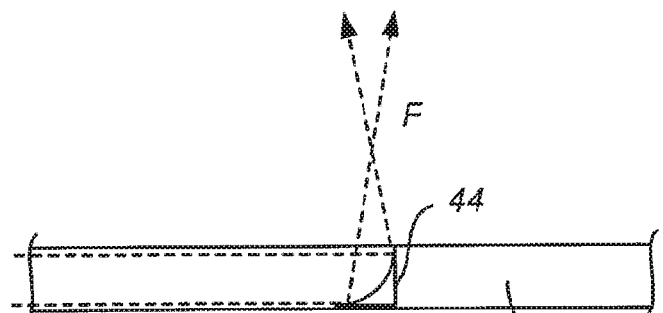
FIGS. 2A and 2B illustrate two alternative arrangements for focusing coherent light from a waveguide into a pressurized liquid stream in the mechanism of FIG. 2.
Figure 2B:
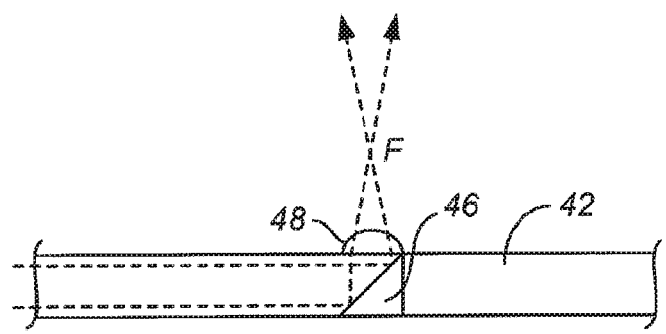

As shown in FIGS. 2A and 2B, the light transmissive fiber 42 includes an element 44 (FIG. 2A) or 46 (FIG. 2B) for transversely or laterally reflecting light transmitted through the fiber so that it may be emitted through the port 34 and into the flowing fluid stream passing therethrough. It will be desirable that the light emitted from the optical waveguide 42 be focused at a point F within the flowing fluid stream so that the light may then be transmitted and propagated through the stream by total internal reflection. Reflective element 44 may have a parabolic or other shaped surface to affect the desired focusing. In contrast, the reflective element 46 may have a flat, non-focusing surface that passes the light through a focusing lens 48, as shown in FIG. 2B.

Figure 3A:
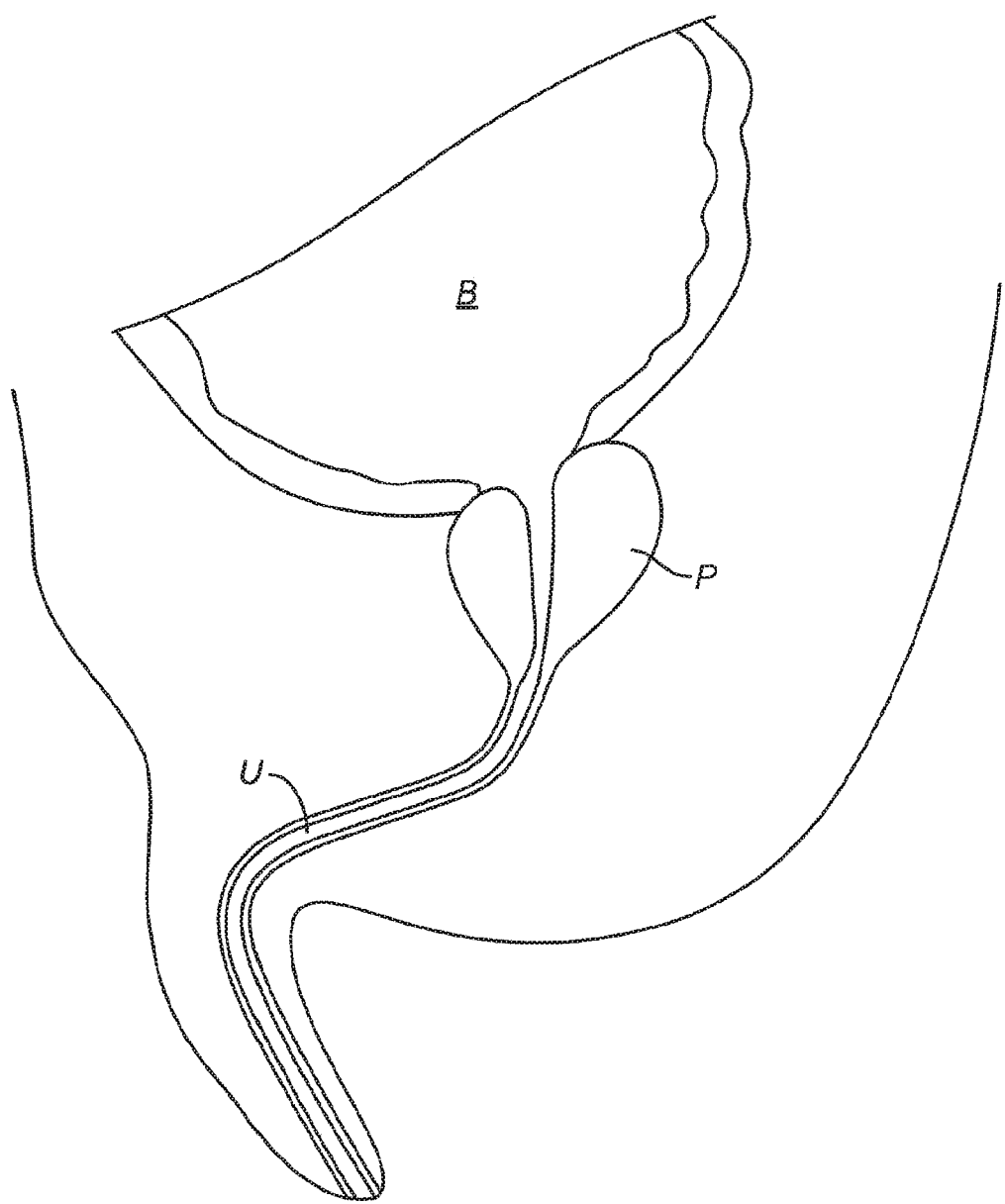
FIGS. 3A-3C illustrate use of the device of FIG. 1 in performing prostatic tissue debulking.
Figure 3B:
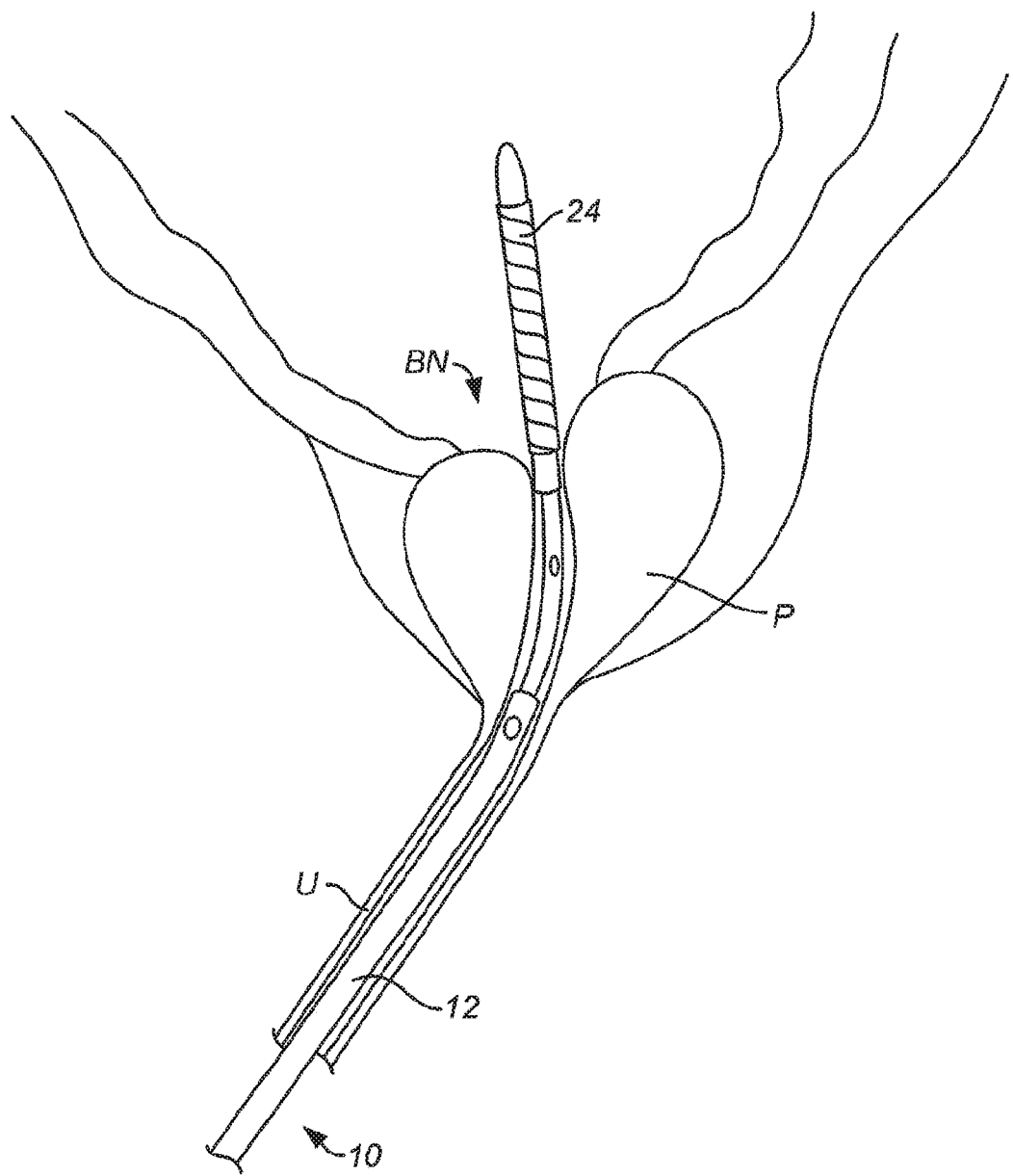
Figure 3C:
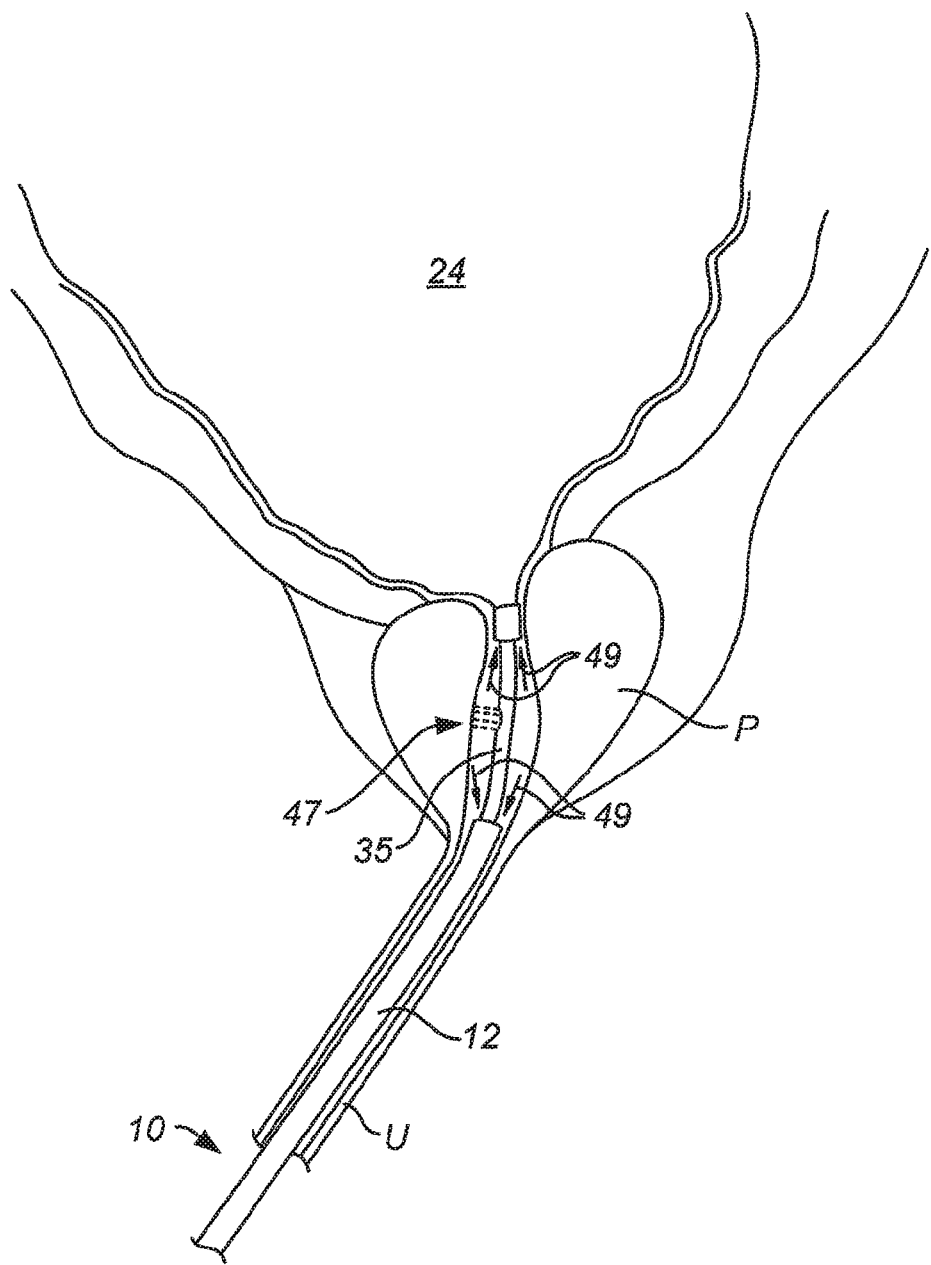

Referring now to FIGS. 3A-3C, the prostatic tissue debulking device 10 is introduced through the male urethra U to a region within the prostate P which is located immediately distal to the bladder B. The anatomy is shown in FIG. 3A. Once the catheter 10 has been positioned so that the anchoring balloon 24 is located just distal of the bladder neck BN (FIG. 3B) the balloon can be inflated, preferably to occupy substantially the entire interior of the bladder, as shown in FIG. 3C. Once the anchoring balloon 24 is inflated, the position of the prostatic tissue debulking device 10 will be fixed and stabilized within the urethra U so that the energy source 20 is positioned within the prostate P. It will be appreciated that proper positioning of the energy source 20 depends only on the inflation of the anchoring balloon 24 within the bladder. As the prostate is located immediately proximal to the bladder neck BN, by spacing the distal end of the energy delivery region very close to the proximal end of the balloon, the delivery region can be properly located, typically being spaced by a distance in the range from 0 mm to 5 mm, preferably from 1 mm to 3 mm from the bladder neck. After the anchoring balloon 24 has been inflated, light and high fluid energy can be delivered into the prostate for debulking as shown by the arrows in FIG. 2, while simultaneously removing the debulked/destroyed tissue and residual fluid by aspiration, typically at both ends of the window, as shown by the arrows 49 in FIG. 3C. Alternatively, the prostate (urethra) can be insufflated or flushed at a pressure greater than that of the aspiration (exhaust) system to enhance tissue and debris collection. Once the energy has been delivered for a time and over a desired surface region, the energy region can be stopped.

As shown in FIG. 3C, the inner fluid delivery tube 35 may be axially translated and/or rotated in order to sweep the fluid/coherent light stream 47 over the interior of the urethra within the prostate P. The energy carried by the fluid/light stream both ablates the prostatic tissue and cauterizes the tissue to limit bleeding after debulking. Once a sufficient volume of tissue has been removed, the fluid stream and light source may be turned off, the balloon 24 deflated, the catheter 10 removed from the urethra.

Referring now to FIGS. 4A-4E, a device 60 constructed in accordance with the principles of the present invention comprises a central shaft 62 having a window 64 near a distal end thereof. A hypotube 66 is carried in a proximal bushing 68 (FIG. 4A) and a threaded region 70 of the hypotube 66 is received within internal threads of the bushing 68. Thus, rotation of the hypotube can axially advance and retract the hypotube relative to the bushing and central shaft 62. Typically, rotation and axial movement of the hypotube 66 relative to the bushing 68 and central shaft 62 is achieved by separately controlling the axial and rotational movement of the hypotube, thereby obviating the need for internal threads and allowing for more versatility of movement within the window 64.

The hypotube 66 carries a laser fiber 72 and includes a lumen 74 which can receive and deliver a water or other fluid jet as will be described in more detail below. The central shaft 62 further includes a balloon inflation lumen 76 and lumen 78 for the suction removal of ablated tissue.

Figure 4A:
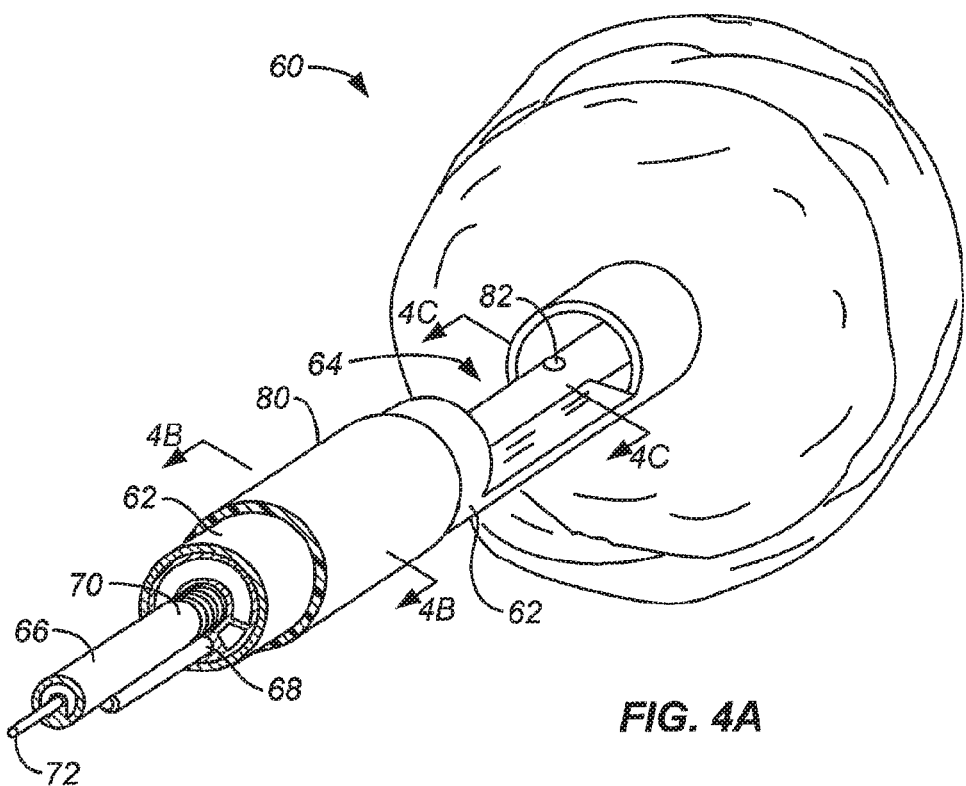
Figure 4B:
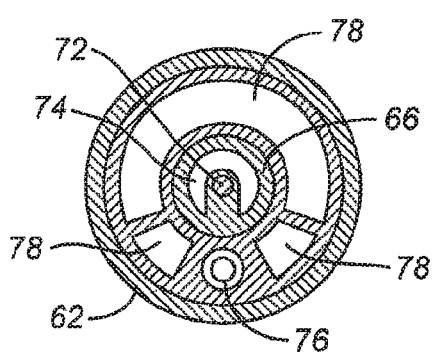
Figure 4C:
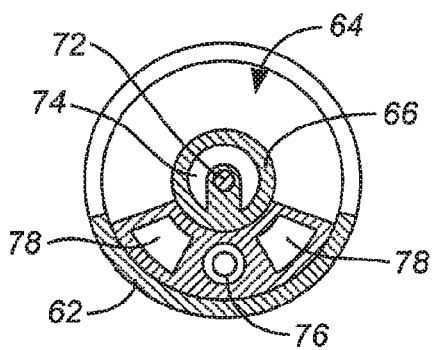

When introduced through the urethra, the device 60 will typically be covered by a sheath 80 as illustrated in FIG. 4D (only a portion of the sheath 80 is shown in FIG. 4A). When fully covered with sheath 80, the window 66 is protected so that it reduces scraping and injury to the urethra as the device is advanced.

Once in place, the sheath 80 will be retracted, exposing the window, as illustrated in FIG. 4E. The hypotube 66 may then be rotated and advanced and/or retracted so that the fluid stream FS which carries the optical energy may be delivered through the delivery port 82. Additionally, a balloon 84 may be inflated in order to anchor the device 60 within the bladder as previously described.

Figure 5:
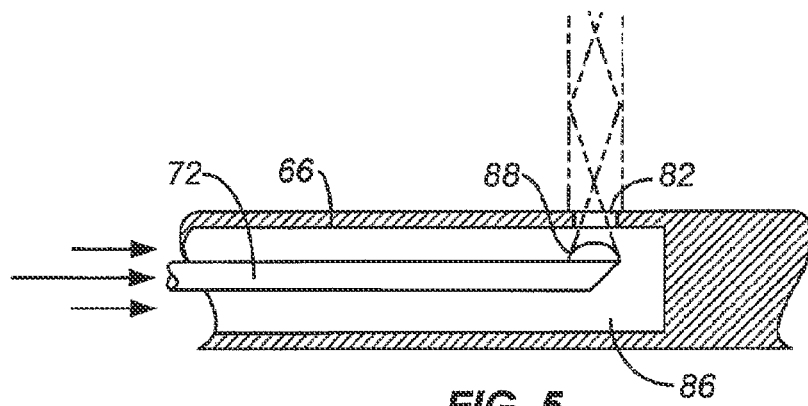
FIG. 5 is a detailed, cross-sectional view of a portion of the rotating and reciprocating fluid and light delivery mechanism of FIGS. 4A-4E.
Figure 6:
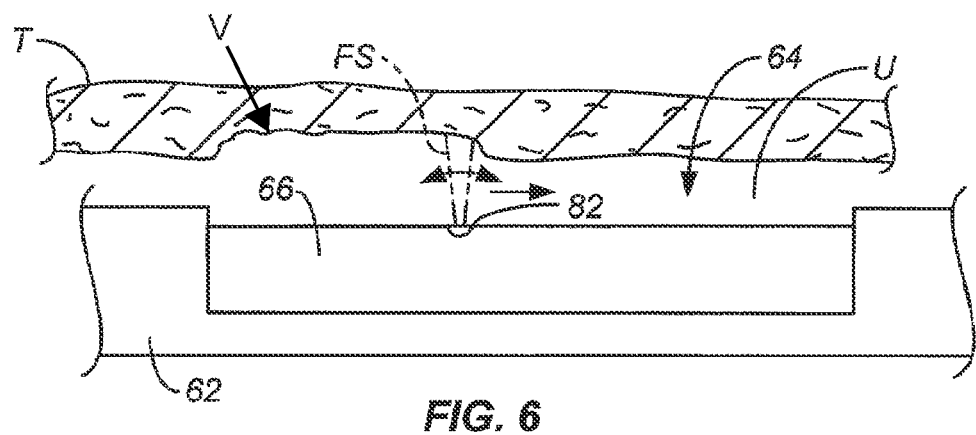
FIG. 6 illustrates use of the device of FIGS. 4A-4E in debulking tissue.

The fiberoptic wave guide 72 is positioned within a lumen 86 of the hypotube 66, as best seen in FIG. 5. Fluid may be delivered through the lumen, surrounding the laser fiber 72 and ejected through the delivery port 82 in a lateral direction. Optical energy delivered through fiber 72 is also reflected laterally and focused by optional lens 88 so that the light is carried by the fluid with internal reflection, as described previously. In use, the hypotube 66 is axially translated within the window 64, as shown in FIG. 6. A fluid stream FS which carries the optical energy is thus directed radially outwardly and against a wall of the body lumen, for example of the urethra U. The energized fluid stream FS is able to ablate a desired depth of tissue T, where the depth can be controlled by the amount of energy delivered and the dwell time or scan time of the fluid stream FS against the tissue. The fluid stream will usually be moved relative to the urethra to remove a pre-defined volume V of prostate tissue T surrounding the urethral lumen in order to partially or fully relieve the compression and/or obstruction.

Figure 7:
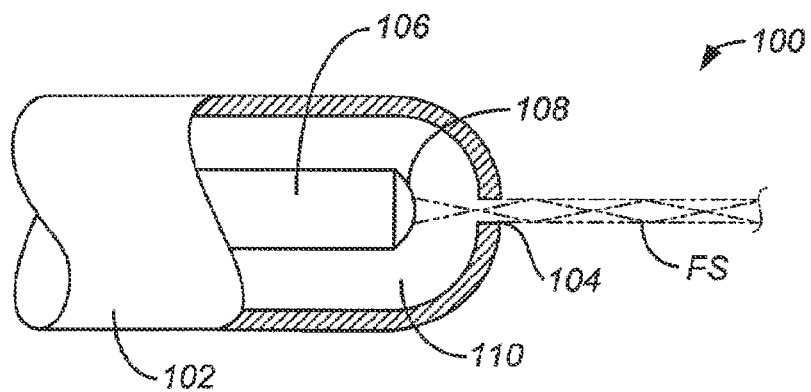
FIG. 7 is a schematic illustration of a device constructed in accordance with the present invention suitable for performing tissue cutting or other procedures where an axial pressurized liquid stream is delivered from a distal tip of the device and carries focused coherent light from a waveguide.
Figure 10:
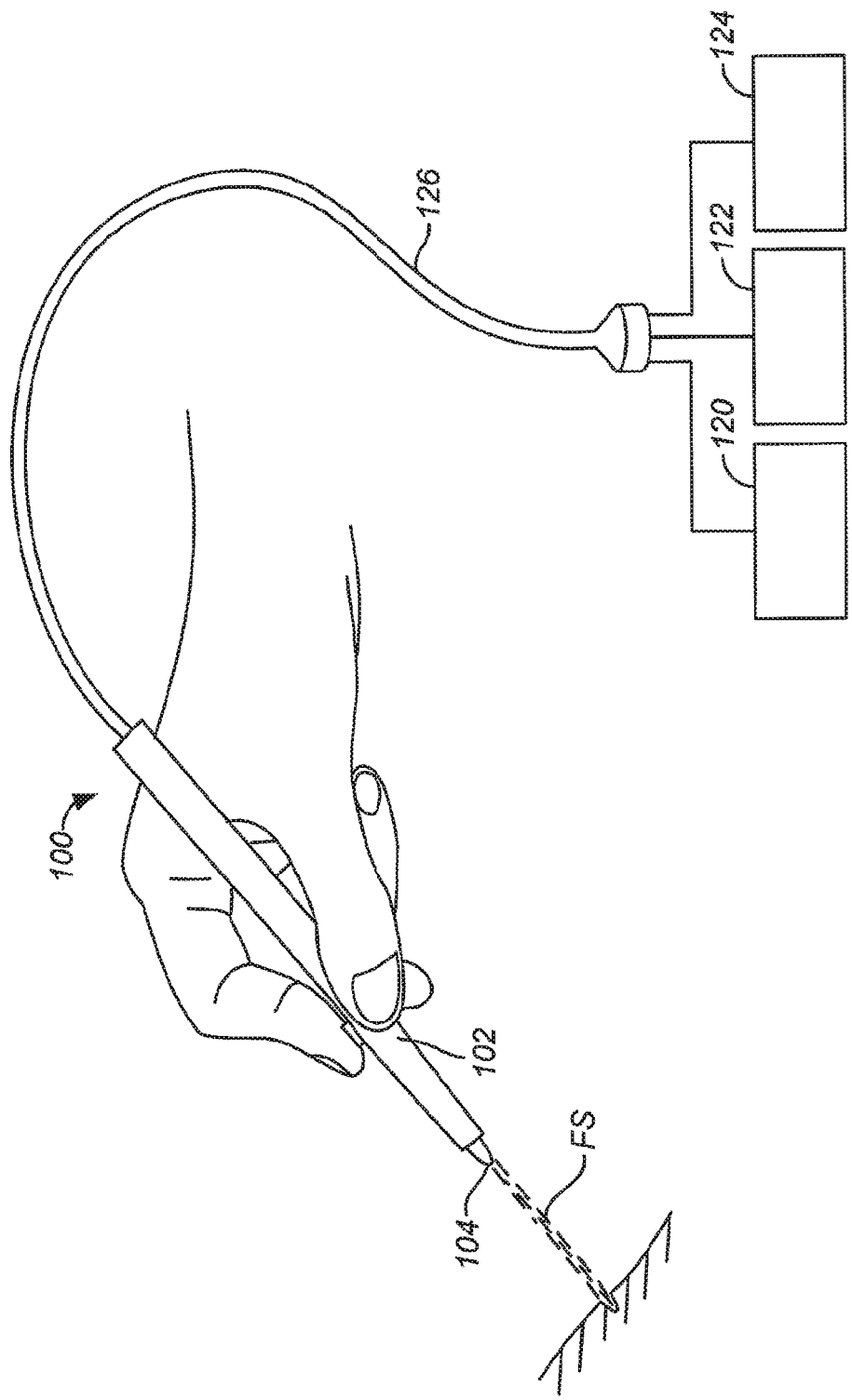
FIG. 10 illustrates use of the device of FIG. 7 as a scalpel for cutting tissue.

As shown in FIG. 7, a handheld device 100 may comprise a shaft 102 having a distal end with a nozzle 104 oriented to deliver a pressurized fluid in an axial stream or water jet FS. A laser fiber 106 is disposed axially within the shaft 102 and terminates in a lens 108 which focuses light into the axial water jet FS. Water or other fluid is delivered under pressure in an annular region 110 of the shaft 102 which surrounds the laser fiber 106 and is enclosed by an outer perimeter of the shaft. The handheld device 100 is capable of delivering an axial water jet or other pressurized fluid stream and is useful for the manual cutting of tissue or bone, as shown in FIG. 10. The handheld device 100 is connected to a pressurized fluid source 120, a light source 122, and control circuitry 124, typically by a connecting cord 126. The user can thus control the fluid pressure, the amount of light energy being introduced into the fluid stream, movement of the nozzle (velocity, direction, limits, etc.) and other aspects of the treatment protocol in addition to the axial and rotational movement parameters using the control circuitry. Optionally, although not illustrated, the nozzle 104 will be adjustable in order to adjust the width and focus of the fluid stream FS in order to allow further flexibility for the treatment. When used for cutting tissue, it can be manipulated much as a scalpel.

Figure 8:
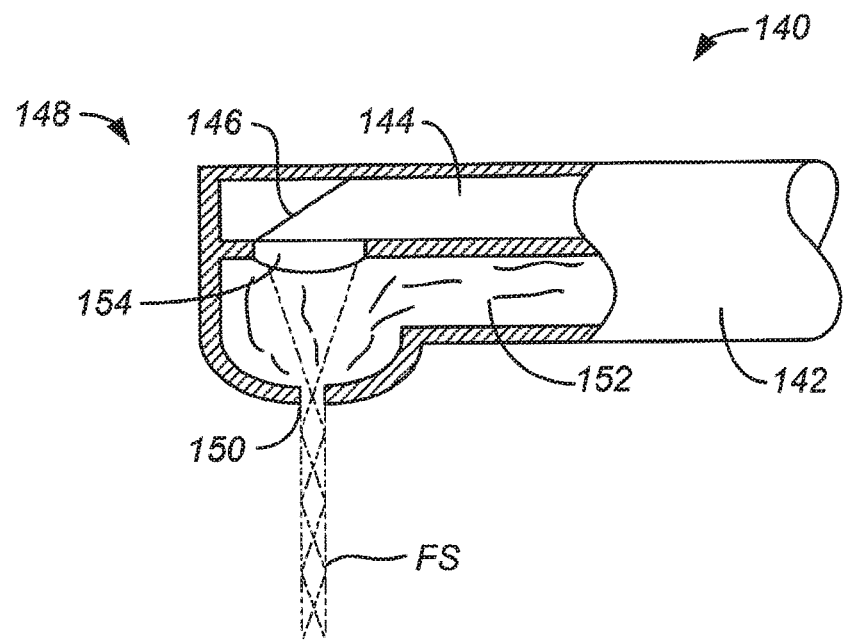
FIG. 8 illustrates another handheld device constructed in accordance with the principles of the present invention, where the pressurized liquid stream carrying the coherent light is directed laterally from the shaft of the device.
Figure 11:
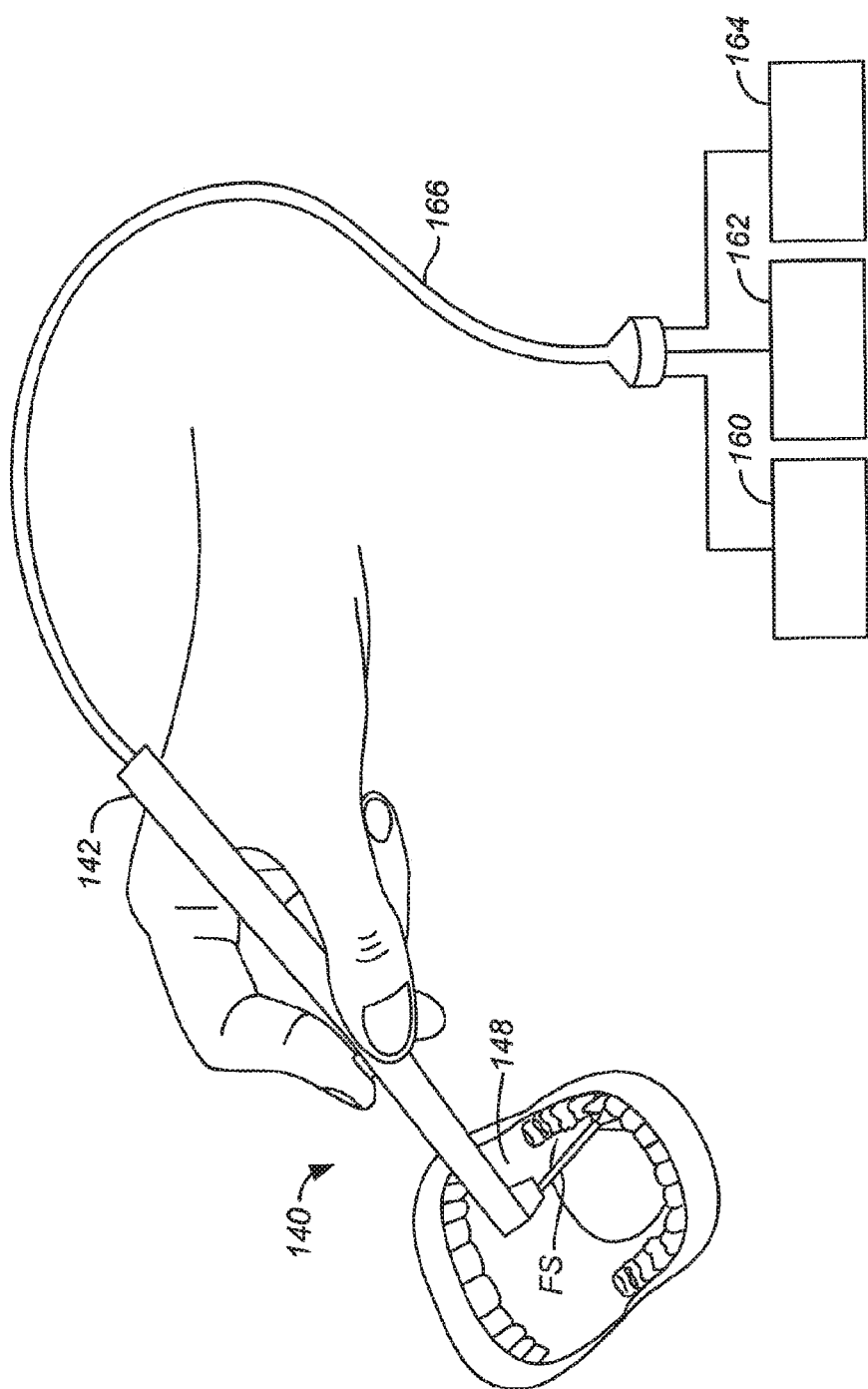
FIG. 11 illustrates the use of the device of FIG. 8 for drilling a tooth.

FIG. 8 illustrates another handheld device 140 where a principle difference with the device of FIG. 7 is that the water jet or other pressurized fluid stream FS is directed in a lateral direction from shaft 142, illustrated as a right angle relative to an axis of the shaft 142. Light is delivered through a laser fiber 144 and reflected, typically by an air mirror 146, or side firing optical fiber, laterally near a distal end 148 of the shaft 142 so that light enters the lateral water jet or other pressurized fluid stream FS, as described previously. The pressurized fluid stream FS is created through a fixed or adjustable nozzle 150 on the side of the shaft 142, where the fluid is delivered under pressure through a lumen or other conduit 152 formed within the shaft 142. As with previous embodiments, a focusing lens 154 is optionally provided to deliver the coherent light from the laser fiber 144 into the water jet or other pressurized fluid stream FS. The device of FIG. 8 may be used for a variety of procedures, such as tooth drilling as illustrated in FIG. 11. The lateral flow handheld device 140 can be held and manipulated by the dentist in a manner similar to conventional dental drills. The distal end 148 of the shaft will be held in the mouth so that the stream FS is directed against the dental surface to be treated. The shaft 142, laser fiber 144, and flow lumen 152 will be connected to a water or other fluid source 160, a suitable laser light source 162, and control circuitry 164 by connecting cable 166.

Figure 9:
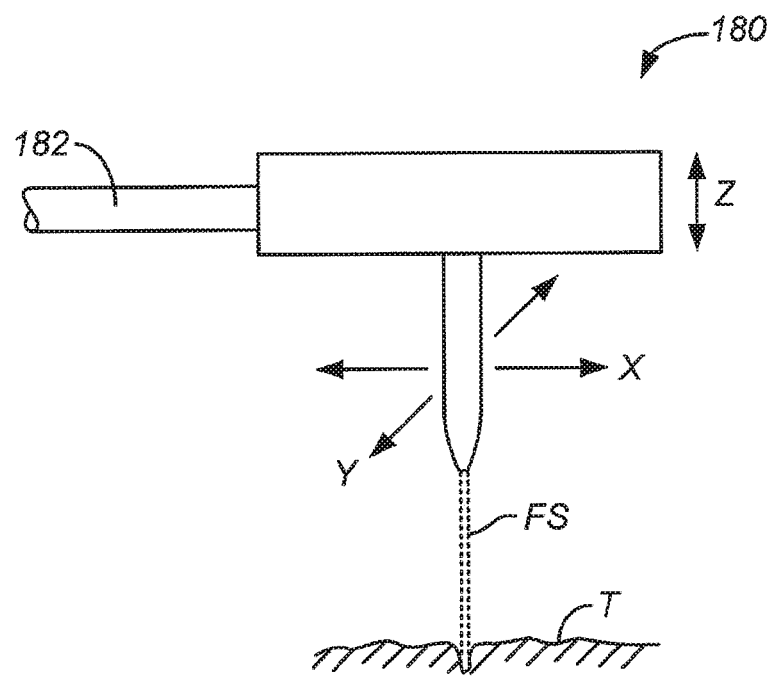
FIG. 9 illustrates a robotically deployed pressurized fluid/coherent light delivery mechanism.

As illustrated in FIG. 9, a scalpel-type device 180 may be attached to a programmable machine arm 182 so that the systems can be used in robotic or other automatic, programmable systems. The programmable machine arm 182 may be suspended over tissue T to be treated, and the water jet or other pressurized fluid stream FS carrying the coherent light is used to cut or incise the tissue, as illustrated. The programmable machine arm may be moved in any of the X, Y, and/or Z directions, where the control is provided by computer or by a manual control system, for example, guided by a joystick or other manipulator.

Figure 12:
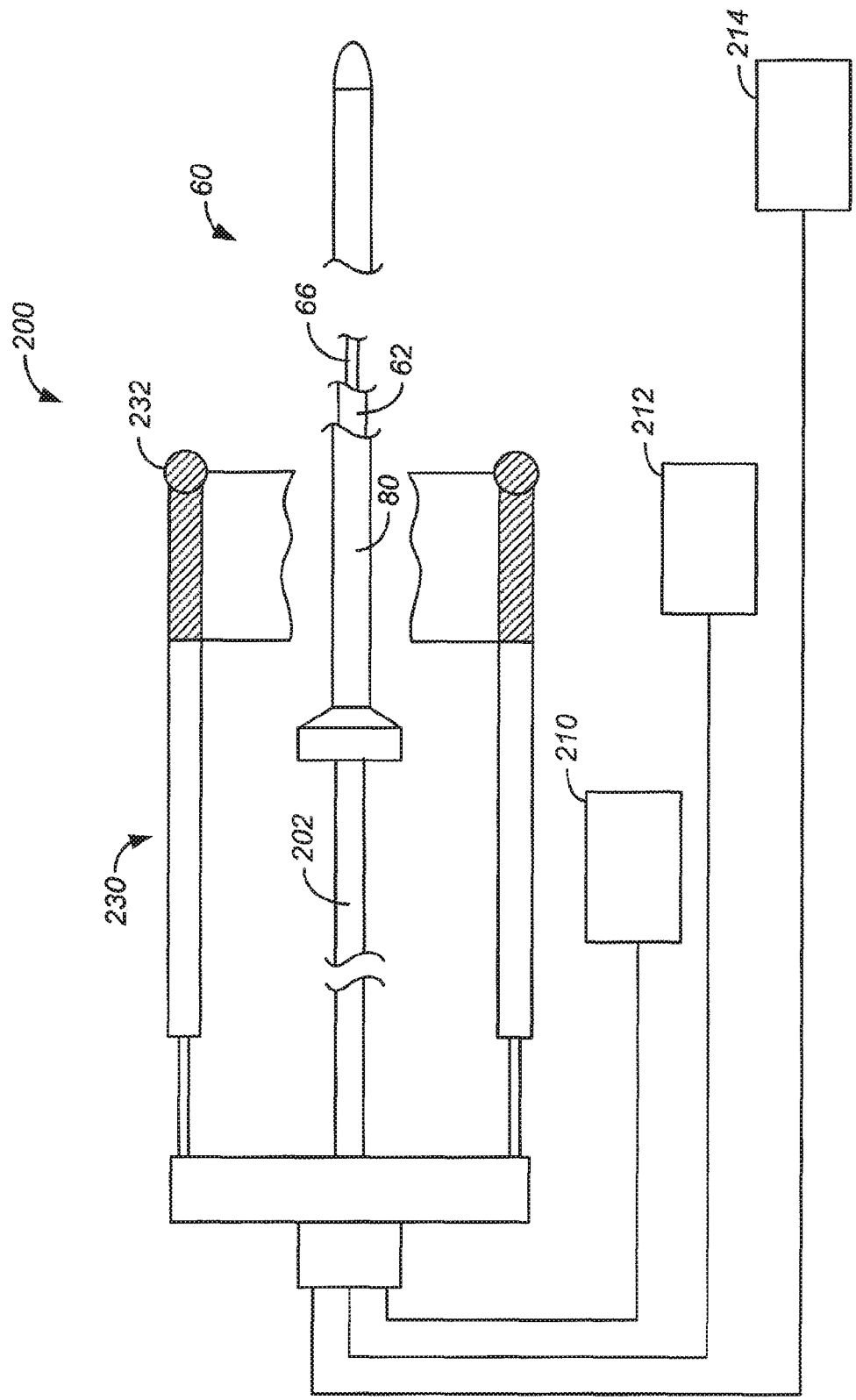
FIG. 12 illustrates a system for deploying a tissue debulking device similar to that illustrated in FIGS. 4A-4E and including a tissue stabilization sheath and schematically illustrating the various drive mechanisms in accordance with the principles of the present invention.

A system 200 for the automatic deployment of the light fluid delivery device 60 of FIGS. 4A-4E is illustrated in FIG. 12. The central shaft 62, hypotube 66, and sheath 80 of the device are connected to a control shaft 202 which in turn is connected to a base unit 204 which includes motors and control circuitry (not shown) for controlling the relative movements of the shaft, hypotube, and sheath. The base unit 204 in turn will be connected to a pressurized fluid source 210, a laser or other optical energy source 212, and an external console or controller 214 which provides an interface for programming and/or manipulating the device 60. In addition to the device 60, the system 200 may include an external anchor frame 230 which can be automatically (or manually) advanced and retracted coaxially over the device 60. The anchor frame 230 typically includes an atraumatic ring 232 for engaging and anchoring the system against tissue after the device has been introduced and the balloon expanded to allow the device to be tensioned.

The apparatus and systems of the present invention may include a number of other optional features. For example, blades or other cutting elements could be included within the waste lumen(s) 78 of the device 60 in order to macerate tissue and other debris as it is being aspirated/evacuated and removed. The device 60 or any of the other configurations of the present invention may optionally be provided with imaging and illumination fibers, cameras, or the like, in order to provide for visual monitoring during the procedure. Optical fibers or cameras may be placed anywhere on the device, optionally within the treatment windows as described before. Means may be provided for keeping the cameras, fibers, lenses, or the like, clean so that good images may be obtained. In all of the above embodiments, instead of employing mirrors, the light may be directed into the fluid stream by bending the light fiber. Additionally, depending on the size of the light fiber and proximity of the fluid nozzle, a focusing lens may or may not be necessary.

While the above is a complete description of the preferred embodiments of the invention, various alternatives, modifications, and equivalents may be used. Therefore, the above description should not be taken as limiting the scope of the invention which is defined by the appended claims.

What is claimed is:

1. A medical method, comprising:
   providing a water jet system, wherein the water jet system comprises a water jet fluid flush tube and an aspiration tube within a sheath;
   endoscopically inserting the water jet system into a patient;
   utilizing an imaging system to provide an image of the water jet system relative to the patient;

applying fluid from the water jet flush tube to create a cutting jet area to break apart tissue;

robotically controlling cutting motion by the water jet fluid flush tube to break apart the tissue by rotating and translating the water jet flush tube relative to the sheath; and using the aspiration tube to remove the broken apart tissue via aspiration.

2. The medical method of claim 1, further comprising attaching the water jet system to an arm.

3. The medical method of claim 2, wherein the arm is a robotic arm, and wherein the robotic arm is coupled to the water jet system via an instrument driver.

4. The medical method of claim 1, wherein the fluid comprises a saline solution.

5. The medical method of claim 1, wherein the applying fluid includes modulating the flow.

6. The medical method of claim 1, wherein a portion of the water jet fluid flush tube and a portion of the aspiration tube are co-axially disposed relative to one another.

7. The medical method of claim 1, wherein the cutting motion automatically resects a predefined volume.

8. The medical method of claim 1, further comprising controlling a flow characteristic of the water jet flush tube to treat the tissue to be broken apart.

9. A medical method, comprising:
providing a water jet system, wherein the water jet system comprises a water jet fluid flush tube and an aspiration tube within a sheath;
endoscopically inserting the water jet system into a patient;
utilizing an imaging system to provide an image of the water jet system relative to the patient;
applying fluid from the water jet flush tube to create a cutting jet area to break apart tissue;
robotically controlling cutting motion by the water jet fluid flush tube to break apart the tissue by rotating and translating the water jet flush tube relative to the sheath;
controlling a flow characteristic of the water jet flush tube to treat the tissue to be broken apart; and
using the aspiration tube to remove the broken apart tissue via aspiration.

10. The medical method of claim 9, further comprising attaching the water jet system to an arm.

11. The medical method of claim 10, wherein the arm is a robotic arm, and wherein the robotic arm is coupled to the water jet system via an instrument driver.

12. The medical method of claim 9, wherein the fluid comprises a saline solution.

13. The medical method of claim 9, wherein the applying fluid includes modulating the flow.

14. The medical method of claim 9, wherein a portion of the water jet fluid flush tube and a portion of the aspiration tube are co-axially disposed relative to one another.

15. The medical method of claim 9, wherein the cutting motion automatically resects a predefined volume.

\* \* \* \* \*